(12) United States Patent
MacDonald et al.

(10) Patent No.: US 12,203,129 B2
(45) Date of Patent: Jan. 21, 2025

(54) FORMULATIONS AND SIGNAL ENCODING AND DECODING METHODS FOR MASSIVELY MULTIPLEXED BIOCHEMICAL ASSAYS

(71) Applicant: ChromaCode, Inc., Carlsbad, CA (US)

(72) Inventors: Christopher MacDonald, San Diego, CA (US); Aditya Rajagopal, Orange, CA (US); Paul Flook, San Diego, CA (US); Yaser Abu-Mostafa, Pasadena, CA (US); Dominic Yurk, Garden Grove, CA (US)

(73) Assignee: ChromaCode, Inc., Carlsbad, CA (US)

( * ) Notice: Subject to any disclaimer, the term of this patent is extended or adjusted under 35 U.S.C. 154(b) by 0 days.

(21) Appl. No.: 16/128,343

(22) Filed: Sep. 11, 2018

(65) Prior Publication Data

US 2020/0010876 A1   Jan. 9, 2020

Related U.S. Application Data

(60) Provisional application No. 62/693,777, filed on Jul. 3, 2018.

(51) Int. Cl.
*C12Q 1/6816* (2018.01)

(52) U.S. Cl.
CPC .................... *C12Q 1/6816* (2013.01)

(58) Field of Classification Search
None
See application file for complete search history.

(56) References Cited

U.S. PATENT DOCUMENTS

| | | | |
|---|---|---|---|
| 5,079,351 A | 1/1992 | Sninsky et al. | |
| 5,538,848 A | 7/1996 | Livak et al. | |
| 5,618,711 A | 4/1997 | Gelfand et al. | |
| 5,677,152 A | 10/1997 | Birch et al. | |
| 5,723,591 A | 3/1998 | Livak et al. | |
| 5,773,258 A | 6/1998 | Birch et al. | |
| 5,789,224 A | 8/1998 | Gelfand et al. | |
| 5,804,375 A | 9/1998 | Gelfand et al. | |
| 5,834,203 A | 11/1998 | Katzir et al. | |
| 5,876,930 A | 3/1999 | Livak et al. | |
| 5,882,856 A | 3/1999 | Shuber | |
| 5,928,862 A | 7/1999 | Morrison | |
| 5,948,360 A | 9/1999 | Rao et al. | |
| 5,981,180 A | 11/1999 | Chandler et al. | |
| 5,994,056 A | 11/1999 | Higuchi | |
| 6,030,787 A | 2/2000 | Livak et al. | |
| 6,057,134 A | 5/2000 | Lader et al. | |
| 6,103,463 A * | 8/2000 | Chetverin ............ | B01J 19/0046 435/6.12 |
| 6,127,155 A | 10/2000 | Gelfand et al. | |
| 6,171,785 B1 | 1/2001 | Higuchi | |
| 6,248,526 B1 | 6/2001 | Weimer | |
| 6,258,569 B1 | 7/2001 | Livak et al. | |
| 6,379,888 B1 | 4/2002 | Nadeau et al. | |
| 6,534,266 B1 | 3/2003 | Singer | |
| 6,534,274 B2 | 3/2003 | Becker et al. | |
| 6,548,259 B2 | 4/2003 | Ward et al. | |
| 6,642,062 B2 | 11/2003 | Kauvar et al. | |
| 6,893,875 B2 | 5/2005 | Tsuji et al. | |
| 7,101,663 B2 | 9/2006 | Godfrey et al. | |
| 7,141,377 B2 | 11/2006 | Gelfand et al. | |
| 7,348,141 B2 | 3/2008 | French et al. | |
| 7,385,043 B1 | 6/2008 | Kramer | |
| 7,410,764 B2 | 8/2008 | Gocke et al. | |
| 7,413,708 B2 | 8/2008 | Mayrand | |
| 7,473,767 B2 | 1/2009 | Dimitrov | |
| 7,507,575 B2 | 3/2009 | Bedingham et al. | |
| 7,575,864 B2 | 8/2009 | Bedzyk et al. | |
| 7,667,024 B2 | 2/2010 | Mao et al. | |
| 7,671,184 B2 | 3/2010 | Haener et al. | |
| 7,709,249 B2 | 5/2010 | Bedingham et al. | |
| 7,767,423 B2 | 8/2010 | Kopreski et al. | |
| 7,771,949 B2 | 8/2010 | Kramer | |
| 7,919,237 B2 | 4/2011 | Dimitrov et al. | |
| 7,919,244 B2 | 4/2011 | Madejon et al. | |
| 7,930,106 B2 | 4/2011 | Carrick | |
| 7,941,279 B2 | 5/2011 | Hwang et al. | |
| 8,039,215 B2 | 10/2011 | Higuchi et al. | |
| 8,148,512 B2 | 4/2012 | Dimitrov et al. | |
| 8,426,132 B2 | 4/2013 | Li et al. | |
| 8,455,184 B2 | 6/2013 | Atchley et al. | |

(Continued)

FOREIGN PATENT DOCUMENTS

| CN | 1172530 A | 2/1998 |
|---|---|---|
| CN | 1936019 A | 3/2007 |

(Continued)

OTHER PUBLICATIONS

Rajagopal, et al. Anal. Chem., vol. 85, pp. 7629-7636, published Jun. 13, 2013.*
Beige, et al. Clinical evaluation of a *Mycobacterium tuberculosis* PCR assay. J Clin Microbiol. Jan. 1995;33(1):90-5.
Chamberlain, et al. Deletion screening of the Duchenne muscular dystrophy locus via multiplex DNA amplification. Nucleic Acids Res. Dec. 9, 1988;16(23):11141-56.
Chapin et al., Rapid microRNA profiling on encoded gel microparticles. Angewandte Chemie International Edition, 50(10):2289-2293, 2011.
Chen, et al. A Homogeneous, ligase-mediated DNA diagnostic test. Genome Research, 1998, vol. 8, pp. 549-556.
Chong, et al. Single-tube multiplex-PCR screen for common deletional determinants of alpha-thalassemia. Blood. Jan. 1, 2000;95(1):360-2.
Chromatogram, 2011, 2 pages. Dorland's illustrated medical dictionary. Retrieved online on Jan. 22, 2014 from «http://www.credoreference.com».

(Continued)

*Primary Examiner* — Narayan K Bhat
(74) *Attorney, Agent, or Firm* — WILSON SONSINI GOODRICH & ROSATI

(57) ABSTRACT

The present disclosure provides methods and compositions for the multiplexed detection of multiple analytes from a sample. Analytes may be nucleic acid analytes. Detection of analytes may comprise contacting one or more sample subsets with hybridization probes, thereby generating one or more cumulative signal measurements capable of detecting the presence of absence of a plurality of analytes.

17 Claims, 11 Drawing Sheets

(56) References Cited

U.S. PATENT DOCUMENTS

| | | |
|---|---|---|
| 8,492,094 B2 | 7/2013 | Dimitrov et al. |
| 8,519,115 B2 | 8/2013 | Webster et al. |
| 8,614,061 B2 | 12/2013 | Brabetz et al. |
| 8,771,955 B2 | 7/2014 | Reed et al. |
| 8,838,394 B2 | 9/2014 | Kartalov et al. |
| 8,877,464 B2 | 11/2014 | Babiel et al. |
| 8,962,250 B2 | 2/2015 | Stanley |
| 9,133,506 B2 | 9/2015 | Katzir et al. |
| 9,222,128 B2 | 12/2015 | Saxonov et al. |
| 9,260,761 B2 | 2/2016 | Tyagi et al. |
| 9,366,632 B2 | 6/2016 | Link et al. |
| 9,422,593 B2 | 8/2016 | Rothmann et al. |
| 9,441,266 B2 | 9/2016 | Larson et al. |
| 9,447,457 B2 | 9/2016 | Chun et al. |
| 9,458,497 B2 | 10/2016 | Hassibi et al. |
| 9,791,372 B2 | 10/2017 | Malik et al. |
| 10,066,263 B2 | 9/2018 | Rajagopal et al. |
| 10,068,051 B2 | 9/2018 | Kartalov et al. |
| 10,770,170 B2 * | 9/2020 | Kartalov .............. C12Q 1/68 |
| 2002/0022273 A1 | 2/2002 | Empedocles et al. |
| 2002/0132260 A1 * | 9/2002 | Erlander ............ C12Q 1/6816 |
| | | 435/6.14 |
| 2002/0146734 A1 | 10/2002 | Ortyn et al. |
| 2003/0134320 A1 * | 7/2003 | Barrus ............ G01N 27/44721 |
| | | 435/6.11 |
| 2003/0148280 A1 | 8/2003 | Harris et al. |
| 2003/0148544 A1 | 8/2003 | Nie et al. |
| 2004/0023207 A1 | 2/2004 | Polansky |
| 2004/0053230 A1 | 3/2004 | Schaffer et al. |
| 2004/0180378 A1 * | 9/2004 | Tozer .................... C07K 14/00 |
| | | 435/7.1 |
| 2004/0191794 A1 | 9/2004 | Weindel et al. |
| 2004/0248082 A1 | 12/2004 | Scallon |
| 2005/0053950 A1 | 3/2005 | Zudaire et al. |
| 2005/0064435 A1 | 3/2005 | Su et al. |
| 2005/0106607 A1 * | 5/2005 | Yin ...................... B01L 3/5085 |
| | | 435/6.11 |
| 2005/0164264 A1 | 7/2005 | Shipwash |
| 2005/0214753 A1 | 9/2005 | Shultz et al. |
| 2005/0250146 A1 | 11/2005 | McMillan |
| 2005/0260640 A1 | 11/2005 | Andersen et al. |
| 2006/0039918 A1 | 2/2006 | Albani et al. |
| 2006/0216708 A1 | 9/2006 | Venema |
| 2007/0072211 A1 | 3/2007 | Newton et al. |
| 2007/0161043 A1 | 7/2007 | Nie et al. |
| 2007/0178485 A1 | 8/2007 | El-Deiry et al. |
| 2007/0231824 A1 | 10/2007 | Chee et al. |
| 2008/0003599 A1 | 1/2008 | Dary et al. |
| 2008/0050737 A1 | 2/2008 | Arieli et al. |
| 2008/0069733 A1 | 3/2008 | Maltezos et al. |
| 2008/0096767 A1 * | 4/2008 | Kohn ................ B01J 19/0046 |
| | | 506/9 |
| 2008/0124705 A1 | 5/2008 | Kramer |
| 2009/0042735 A1 | 2/2009 | Blair et al. |
| 2009/0048785 A1 | 2/2009 | Katzir et al. |
| 2009/0062129 A1 | 3/2009 | McKernan et al. |
| 2010/0015607 A1 | 1/2010 | Geiss et al. |
| 2010/0041092 A1 | 2/2010 | Lin et al. |
| 2010/0047924 A1 | 2/2010 | Webster et al. |
| 2010/0112710 A1 | 5/2010 | Geiss et al. |
| 2010/0120043 A1 * | 5/2010 | Sood ..................... G01N 33/542 |
| | | 435/6.11 |
| 2010/0129792 A1 | 5/2010 | Makrigiorgos |
| 2010/0151443 A1 | 6/2010 | Xiang et al. |
| 2010/0159447 A1 | 6/2010 | Li et al. |
| 2010/0210472 A1 | 8/2010 | Empedocles et al. |
| 2010/0233686 A1 | 9/2010 | Higuchi et al. |
| 2010/0248257 A1 | 9/2010 | Jacobsen et al. |
| 2010/0261026 A1 | 10/2010 | Ferree et al. |
| 2010/0267064 A1 | 10/2010 | Kartalov et al. |
| 2010/0273173 A1 | 10/2010 | Hirai et al. |
| 2010/0317005 A1 | 12/2010 | Hardin et al. |
| 2010/0324834 A1 | 12/2010 | Treptow et al. |
| 2011/0104684 A1 | 5/2011 | Hooper |
| 2011/0151459 A1 | 6/2011 | Rothmann et al. |
| 2011/0151550 A1 | 6/2011 | Sagner et al. |
| 2011/0171658 A1 | 7/2011 | Carrick |
| 2011/0183884 A1 | 7/2011 | Miller et al. |
| 2011/0207623 A1 | 8/2011 | Dimitrov et al. |
| 2011/0223602 A1 | 9/2011 | Whitman et al. |
| 2011/0237459 A1 | 9/2011 | Nova et al. |
| 2012/0003646 A1 | 1/2012 | Joo et al. |
| 2012/0040349 A1 | 2/2012 | Von Lode et al. |
| 2012/0040352 A1 | 2/2012 | Wangh et al. |
| 2012/0045756 A1 | 2/2012 | Rothmann et al. |
| 2012/0077195 A1 | 3/2012 | Li et al. |
| 2012/0077692 A1 | 3/2012 | Hassibi et al. |
| 2012/0101740 A1 | 4/2012 | Orpana et al. |
| 2012/0122704 A1 | 5/2012 | Atchley et al. |
| 2012/0141995 A1 | 6/2012 | Li et al. |
| 2012/0164652 A1 * | 6/2012 | Clemens ............... C12Q 1/6851 |
| | | 435/6.12 |
| 2012/0171677 A1 | 7/2012 | Ludowise |
| 2012/0184017 A1 | 7/2012 | Chatterjee |
| 2012/0190030 A1 | 7/2012 | Chun et al. |
| 2012/0196283 A1 | 8/2012 | Babiel et al. |
| 2012/0244534 A1 | 9/2012 | Ching et al. |
| 2012/0252014 A1 | 10/2012 | Loeffert et al. |
| 2012/0252015 A1 * | 10/2012 | Hindson ............... C12Q 1/6883 |
| | | 435/6.11 |
| 2012/0252017 A1 | 10/2012 | Reed et al. |
| 2012/0258457 A1 | 10/2012 | Jarosch et al. |
| 2012/0302448 A1 | 11/2012 | Hutchison et al. |
| 2013/0017971 A1 | 1/2013 | Geiss et al. |
| 2013/0040841 A1 | 2/2013 | Saxonov et al. |
| 2013/0078626 A1 | 3/2013 | Wasserstrom et al. |
| 2013/0116780 A1 | 5/2013 | Miller et al. |
| 2013/0178378 A1 * | 7/2013 | Hatch .................... C12Q 1/686 |
| | | 506/9 |
| 2013/0209997 A1 | 8/2013 | Whitney et al. |
| 2013/0261019 A1 | 10/2013 | Lin et al. |
| 2013/0288244 A1 | 10/2013 | Deciu et al. |
| 2014/0004520 A1 * | 1/2014 | Mohapatra ........... C12Q 1/6851 |
| | | 435/6.11 |
| 2014/0038195 A1 | 2/2014 | Malik et al. |
| 2014/0171341 A1 | 6/2014 | Jouvenot et al. |
| 2014/0213471 A1 | 7/2014 | Rajagopal et al. |
| 2014/0274774 A1 | 9/2014 | Li et al. |
| 2015/0057178 A1 | 2/2015 | Kartalov et al. |
| 2015/0072887 A1 | 3/2015 | Chun et al. |
| 2015/0111776 A1 | 4/2015 | Chen |
| 2015/0140554 A1 | 5/2015 | Snyder et al. |
| 2015/0211054 A1 * | 7/2015 | Kostem ................ C12Q 1/6869 |
| | | 506/9 |
| 2015/0275295 A1 | 10/2015 | Wang et al. |
| 2016/0040249 A1 * | 2/2016 | Ceppi .................... C12Q 1/6886 |
| | | 506/9 |
| 2016/0040256 A1 | 2/2016 | Chen et al. |
| 2016/0108464 A1 | 4/2016 | Saxonov et al. |
| 2016/0201122 A1 * | 7/2016 | Bushkin ............... C12Q 1/6841 |
| | | 435/6.11 |
| 2016/0273048 A1 | 9/2016 | Roperch |
| 2016/0281130 A1 * | 9/2016 | Dahl .................... C12Q 1/6816 |
| 2017/0145490 A1 | 5/2017 | Chiu et al. |
| 2017/0314073 A1 | 11/2017 | Grömminger et al. |
| 2017/0362636 A1 | 12/2017 | Rajagopal et al. |
| 2018/0030551 A1 | 2/2018 | Rajagopal et al. |
| 2018/0052110 A1 | 2/2018 | Malik et al. |
| 2018/0057864 A1 | 3/2018 | Jacky et al. |
| 2019/0002963 A1 | 1/2019 | Rajagopal |
| 2019/0032112 A1 | 1/2019 | Rajagopal et al. |
| 2019/0112636 A1 | 4/2019 | Rajagopal et al. |
| 2019/0233882 A1 | 8/2019 | Jacky et al. |
| 2020/0087709 A1 | 3/2020 | Bracht et al. |

FOREIGN PATENT DOCUMENTS

| | | |
|---|---|---|
| CN | 101570782 A | 11/2009 |
| CN | 101646786 A | 2/2010 |
| CN | 101831496 A | 9/2010 |
| CN | 102269759 A | 12/2011 |
| CN | 102439171 A | 5/2012 |

(56) References Cited

FOREIGN PATENT DOCUMENTS

| | | |
|---|---|---|
| CN | 102559868 A | 7/2012 |
| CN | 102576390 A | 7/2012 |
| CN | 103293299 A | 9/2013 |
| CN | 104404162 A | 3/2015 |
| CN | 106148521 A | 11/2016 |
| CN | 106636409 A | 5/2017 |
| CN | 104662172 B | 7/2018 |
| EP | 0519338 A1 | 12/1992 |
| EP | 1087020 A2 | 3/2001 |
| EP | 1448581 B1 | 11/2008 |
| EP | 2224017 A1 | 9/2010 |
| EP | 1963531 B1 | 9/2011 |
| EP | 1629108 B1 | 12/2014 |
| GB | 2526445 A | 11/2015 |
| JP | 2005508493 A | 3/2005 |
| JP | 2007525184 A | 9/2007 |
| WO | WO-9624044 A1 | 8/1996 |
| WO | WO-9746714 A1 | 12/1997 |
| WO | WO-9919515 A1 | 4/1999 |
| WO | WO-9952708 A1 | 10/1999 |
| WO | WO-0107640 A2 | 2/2001 |
| WO | WO-0159144 A1 | 8/2001 |
| WO | WO-02056014 A2 | 7/2002 |
| WO | WO-03002979 A2 | 1/2003 |
| WO | WO-03003015 A2 | 1/2003 |
| WO | WO-03020967 A1 | 3/2003 |
| WO | WO-02056014 A3 | 10/2003 |
| WO | WO-2004087950 A2 | 10/2004 |
| WO | WO-2004099434 A2 | 11/2004 |
| WO | WO-2006079049 A2 | 7/2006 |
| WO | WO-2006138679 A2 | 12/2006 |
| WO | WO-2007076128 A2 | 7/2007 |
| WO | WO-2007076129 A2 | 7/2007 |
| WO | WO-2007076132 A2 | 7/2007 |
| WO | WO-2007076132 A3 | 9/2007 |
| WO | WO-2007076128 A3 | 11/2007 |
| WO | WO-2007139766 A2 | 12/2007 |
| WO | WO-2007076129 A3 | 3/2008 |
| WO | WO-2008118998 A2 | 10/2008 |
| WO | WO-2008124847 A2 | 10/2008 |
| WO | WO-2007139766 A3 | 12/2008 |
| WO | WO-2008124847 A3 | 2/2009 |
| WO | WO-2009036514 A2 | 3/2009 |
| WO | WO-2009081967 A1 | 7/2009 |
| WO | WO-2010007355 A1 | 1/2010 |
| WO | WO-2010013017 A1 | 2/2010 |
| WO | WO-2010017543 A1 | 2/2010 |
| WO | WO-2010019826 A1 | 2/2010 |
| WO | WO-2010075413 A1 | 7/2010 |
| WO | WO-2010128206 A1 | 11/2010 |
| WO | WO-2011047087 A2 | 4/2011 |
| WO | WO-2011047087 A3 | 8/2011 |
| WO | WO-2011100541 A2 | 8/2011 |
| WO | WO-2011116088 A2 | 9/2011 |
| WO | WO-2011100541 A3 | 1/2012 |
| WO | WO-2011116088 A3 | 2/2012 |
| WO | WO-2012056227 A2 | 5/2012 |
| WO | WO-2012058638 A2 | 5/2012 |
| WO | WO-2012106428 A2 | 8/2012 |
| WO | WO-2012135340 A2 | 10/2012 |
| WO | WO-2012058638 A3 | 12/2012 |
| WO | WO-2012135340 A3 | 12/2012 |
| WO | WO-2013096851 A1 | 6/2013 |
| WO | WO-2013116780 A1 | 8/2013 |
| WO | WO-2014022827 A1 | 2/2014 |
| WO | WO-2014116884 A1 | 7/2014 |
| WO | WO-2014149480 A1 | 9/2014 |
| WO | WO-2014164874 A2 | 10/2014 |
| WO | WO-2015147370 A1 | 10/2015 |
| WO | WO 2016/154600 A1 * | 9/2016 ............ C12Q 1/68 |
| WO | WO-2016172632 A2 | 10/2016 |
| WO | WO-2017139354 A1 | 8/2017 |
| WO | WO-2017173035 A1 | 10/2017 |
| WO | WO-2017218777 A1 | 12/2017 |
| WO | WO-2018081178 A1 | 5/2018 |
| WO | WO-2019006023 A1 | 1/2019 |
| WO | WO-2019079204 A1 | 4/2019 |
| WO | WO-2019169043 A1 | 9/2019 |
| WO | WO-2019204357 A1 | 10/2019 |
| WO | WO-2019236447 A1 | 12/2019 |
| WO | WO-2020010137 A1 | 1/2020 |
| WO | WO-2020014388 A1 | 1/2020 |
| WO | WO-2020051521 A1 | 3/2020 |
| WO | WO-2021211613 A1 | 10/2021 |
| WO | WO-2023014898 A1 | 2/2023 |

OTHER PUBLICATIONS

Chun, et al. Dual priming oligonucleotide system for the multiplex detection of respiratory viruses and SNP genotyping of CYP2C19 gene. Nucleic Acids Res. 2007;35(6):e40. Epub Feb. 7, 2007.

Co-pending U.S. Appl. No. 15/914,356, filed Mar. 7, 2018.

Craig, et al. Ordering of cosmid clones covering Herpes simplex virus type I (HSV-I) genome: a test case for fingerprinting by hybridisation. Nucleic Acids Research, 1990, vol. 18, pp. 2653-2660.

Dos Santos, et al. A simple one-step real-time RT-PCR for diagnosis of dengue virus infection. J Med Virol. Aug. 2008;80(8):1426-33. doi: 10.1002/jmv.21203.

El-Hajj, et al. Detection of rifampin resistance in *Mycobacterium tuberculosis* in a single tube with molecular beacons. J Clin Microbiol. Nov. 2001;39(11):4131-7.

EMBL-Bank: AJ303204. http://www.ebi.ac.uk/Tools/dbfetch/emblfetch?db=embl&id=AJ303204&format=default&style=default&Retrieve=Retrieve. Accessed Feb. 2012.

EMBL-Bank: GQ395623. http://www.ebi.ac.uk/Tools/dbfetch/emblfetch?db=embl&id=GQ395623&format=default&style=default&Retrieve=Retrieve. Accessed Feb. 2012.

European Patent Application No. 13744261.2 Extended European Search Report dated May 3, 2016.

Evans et al. Digital PCR for Noninvasive Detection of Aneuploidy: Power Analysis Equations for Feasibility. Fetal Diagn. Ther. 31:244-247(2012).

Fodor, et al. Multiplexed biochemical assays with biological chips. Nature. Aug. 5, 1993;364(6437):555-6.

Fortina, et al. Digital mRNA profiling. Nat Biotechnol. Mar. 2008;26(3):293-4. doi: 10.1038/nbt0308-293.

Gandelman, et al., Novel Bioluminescent Quantitative Detection of Nucleic Acid Amplification in Real-Time, PLoS One, 2010, 5(11):e14155, 14 pages.

GenBank: M93130.1. Dengue type 3 virus complete genome RNA, complete cds. http://www.ncbi.nlm.nih.gov/nuccore/M93130. Accessed Feb. 2012.

Hartman, et al. Development of a novel internal positive control for Taqman based assays. Mol Cell Probes. Feb. 2005;19(1):51-9. Epub Dec. 10, 2004.

Heidari, et al. Detection of Plasmodium falciparum Directly from Blood Samples Using the Polymerase Chain Reaction. Journal of Sciences, Islamic Republic of Iran. 2005 16(1):21-24.

Henegariu, et al. Multiplex PCR: critical parameters and step-by-step protocol. Biotechniques. Sep. 1997;23(3):504-11.

HIV databases. http://www.hiv.lanl.gov/content/index. Accessed Feb. 2012.

Holland, et al., Detection of specific polymerase chain reaction product by utilizing the 5' to 3' exonuclease activity of Thermus aquaticus DNA polymerase. PNAS (USA) 88:7276-7280, 1991.

Horejsh, et al. A molecular beacon, bead-based assay for the detection of nucleic acids by flow cytometry. Nucleic Acids Res. Jan. 19, 2005;33(2):e13.

Huang, et al. Identification of 8 foodborne pathogens by multicolor combinational probe coding technology in a single real-time PCR. Clin Chem. Oct. 2007;53(10):1741-8. Epub Aug. 10, 2007.

Huang, et al. Multicolor combinatorial probe coding for real-time PCR. PLoS One. Jan. 14, 2011;6(1):e16033. doi: 10.1371/journal.pone.0016033.

International Search Report and Written Opinin dated Nov. 16, 2017 for International PCT Patent Application No. PCT/US2017/37682.

(56) References Cited

OTHER PUBLICATIONS

International search report and written opinion dated Apr. 12, 2013 for PCT/US2013/024509.
International search report and written report dated Jun. 22, 2017 for PCT Application No. PCT/US2017/24933.
Jothikumar, et al. Design of FRET-TaqMan probes for multiplex real-time PCR using an internal positive control. Biotechniques. Jun. 2009;46(7):519-24. doi: 10.2144/000113127.
Klostranec et al., Convergence of quantum dot barcodes with microfluidics and signal processing for multiplexed high-throughout infectious disease diagnostics. Nano Letters, 7(9):2812-2818, 2007.
Kuhn, et al. Hybridization of DNA and PNA molecular beacons to single-stranded and double-stranded DNA targets. J Am Chem Soc. Feb. 13, 2002;124(6):1097-103.
Lao, et al. Multiplexing RT-PCR for the detection of multiple miRNA species in small samples. Biochem Biophys Res Commun. Apr. 28, 2006;343(1):85-9. Epub Feb. 28, 2006.
Lee, et al. Novel multiplex PCR using dual-priming oligonucleotides for detection and discrimination of the *Mycobacterium tuberculosis* complex and M. bovis BCG. J Clin Microbiol. Dec. 2010;48(12):4612-4. doi: 10.1128/JCM.00872-10. Epub Oct. 13, 2010.
Lee, et al. Seven-color, homogeneous detection of six PCR products. Biotechniques. Aug. 1999;27(2):342-9.
Li et al., Multiplexed detection of pathogen DNA with DNA-based fluorescence nanobarcodes. Nature Biotechnology, 23(7):885-889, 2005.
Liew, et al. Validating a custom multiplex ELISA against individual commercial immunoassays using clinical samples. Biotechniques. Mar. 2007;42(3):327-8, 330-3.
Lin et al., Self-assembled combinatorial encoding nanoarrays for multiplexed biosensing. Nano Letters, 7(2):507-512, 2007.
Livak, et al. Oligonucleotides with fluorescent dyes at opposite ends provide a quenched probe system useful for detecting PCR product and nucleic acid hybridization. PCR Methods Appl. Jun. 1995;4(6):357-62.
Morrison, et al. Two-color ratio-coding of chromosome targets in fluorescence in situ hybridization: quantitative analysis and reproducibility. Cytometry. Apr. 1, 1997;27(4):314-26.
Noordhoek, et al. Sensitivity and specificity of PCR for detection of *Mycobacterium tuberculosis*: a blind comparison study among seven laboratories. J Clin Microbiol. Feb. 1994;32(2):277-84.
Notice of allowance dated Jun. 2, 2014 for U.S. Appl. No. 13/756,760.
Office action dated Jan. 24, 2014 for U.S. Appl. No. 13/756,760.
Office action dated Jun. 6, 2017 for U.S. Appl. No. 14/451,876.
Office action dated Nov. 23, 2016 for U.S. Appl. No. 14/451,876.
Oliveira, et al. Multiplex PCR strategy for rapid identification of structural types and variants of the mec element in methicillin-resistant *Staphylococcus aureus*. Antimicrob Agents Chemother. Jul. 2002;46(7):2155-61.
Ou, et al. DNA amplification for direct detection of HIV-1 in DNA of peripheral blood mononuclear cells. Science. Jan. 15, 1988;239(4837):295-7.
Paton, et al. Detection and characterization of Shiga toxigenic *Escherichia coli* by using multiplex PCR assays for stx1, stx2, eaeA, enterohemorrhagic *E. coli* hlyA, rfbO111, and rfbO157. J Clin Microbiol. Feb. 1998;36(2):598-602.
Patterson, et al. Detection of HIV-1 DNA and messenger RNA in individual cells by PCR-driven in situ hybridization and flow cytometry. Science. May 14, 1993;260(5110):976-9.
Petersen, et al. Short PNA molecular beacons for real-time PCR allelic discrimination of single nucleotide polymorphisms. Mol Cell Probes. Apr. 2004;18(2):117-22.
Plasmodium falciparum (Plasmodium falciparum) Genome Browser Gateway. http://microbes.ucsc.edu/cgi-bin/hgGateway?hgsid=612764&clade=eukaryota-protista&org=0&db=0. Accessed Feb. 2012.
Ptak, et al. Inhibition of human immunodeficiency virus type 1 replication in human cells by Debio-025, a novel cyclophilin binding agent. Antimicrob Agents Chemother. Apr. 2008;52(4):1302-17. doi: 10.1128/AAC.01324-07. Epub Jan. 22, 2008.
Rosenstraus, et al. An internal control for routine diagnostic PCR: design, properties, and effect on clinical performance. J Clin Microbiol. Jan. 1998;36(1):191-7.
Roth, et al. Feasibility and efficacy of routine PCR screening of blood donations for hepatitis C virus, hepatitis B virus, and HIV-1 in a blood-bank setting. Lancet. Jan. 30, 1999;353(9150):359-63.
Sambrook, et al. Molecular Cloning: A Laboratory Manual. 2nd Edition, 1989.
Sanger, et al. DNA sequencing with chain-terminating inhibitors. Proc Natl Acad Sci U S A. Dec. 1977;74(12):5463-7.
U.S. Appl. No. 15/623,974 Notice of Allowance dated Jul. 3, 2018.
Hudecova, I. et al. Maternal Plasma Fetal DNA Fractions in Pregnancies with Low and High Risks for Fetal Chromosomal Aneuploidies. PLoS ONE 9(2): e88484.
Speicher, et al. Karyotyping human chromosomes by combinatorial multi-fluor FISH. Nat Genet. Apr. 1996;12(4):368-75.
Tirasophon, et al. A novel detection of a single Plasmodium falciparum in infected blood. Biochem Biophys Res Commun. Feb. 28, 1991;175(1):179-84.
Tyagi, et al. Multicolor molecular beacons for allele discrimination. Nat Biotechnol. Jan. 1998;16(1):49-53.
Tyagi, et al. Wavelength-shifting molecular beacons. Nat Biotechnol. Nov. 2000;18(11):1191-6.
Urdea, et al. Requirements for high impact diagnostics in the developing world. Nature. Nov. 23, 2006;444 Suppl 1:73-9.
U.S. Appl. No. 15/677,772 Final Office Action Mailed Jun. 7, 2018.
U.S. Appl. No. 15/677,772 Non-Final Office Action Mailed Feb. 8, 2018.
U.S. Appl. No. 15/892,245 Preinterview First Interview Office Action Mailed May 11, 2018.
U.S. Appl. No. 14/451,876 Notice of Allowance dated Jul. 11, 2018.
U.S. Appl. No. 14/451,876 Notice of Allowance dated Jun. 14, 2018.
U.S. Appl. No. 15/623,974 Office Action dated Feb. 22, 2018.
U.S. Appl. No. 15/677,772 Office Action dated Feb. 8, 2018.
Vet, et al. Multiplex detection of four pathogenic retroviruses using molecular beacons. Proc Natl Acad Sci U S A. May 25, 1999;96(11):6394-9.
Wang, et al. Locked nucleic acid molecular beacons. J Am Chem Soc. Nov. 16, 2005;127(45):15664-5.
Waters, et al. Microchip device for cell lysis, multiplex PCR amplification, and electrophoretic sizing. Anal Chem. Jan. 1, 1998;70(1):158-62.
Weidmann, et al. Rapid detection of herpes simplex virus and varicella-zoster virus infections by real-time PCR. J Clin Microbiol. Apr. 2003;41(4):1565-8.
Wiese, et al. Simultaneous multianalyte ELISA performed on a microarray platform. Clin Chem. Aug. 2001;47(8):1451-7.
Xu et al., Multiplexed SNP genotyping using the Qbead system: a quantum dot-encoded microspere-based assay. Nucleic Acids Research, 31(8):e43, 2003.
Yang, L. et al. A novel universal real-time PCR system using the attached universal duplex probes for quantitative analysis of nucleic acids. BMC Molecular Biology, 9:54 (1-13) Jun. 4, 2008.
Zhang, et al. A novel real-time quantitative PCR method using attached universal template probe. Nucleic Acids Res. Oct. 15, 2003;31(20):e123(pp. 1-8).
Zhang, et al. Novel Multiplex PCR Assay for Characterization and Concomitant Subtyping of Staphylococcal Cassette Chromosome mec Types I to V in Methicillin-Resistant *Staphylococcus aureus*. J Clin Microbiol. Oct. 2005;43(10):5026-33.
International Application No. PCT/US18/39846 International Search Report and Written Opinion Mailed Sep. 14, 2018.
Saiki, et al. Primer-directed enzymatic amplification of DNA with a thermostable DNA polymerase. Science, 239(4839):487-491 (Jan. 29, 1988).
Blacket et al. Universal primers for fluorescent labeling of PCR fragments—an efficient and cost-effective approach to genotyping by fluorescence. Molecular Ecology Resources 12(3):456-463 (2012) Epub Jan. 24, 2012.
Co-pending U.S. Appl. No. 16/537,415, filed Aug. 9, 2019.

(56) References Cited

OTHER PUBLICATIONS

EP17814096.8 Extended European Search Report dated Dec. 2, 2019.
EP1818686.9 Extended Search Report dated Jul. 23, 2019.
European Office Action for Patent Application No. EP13824744.0 dated Nov. 6, 2018.
Extended European Search Report for Patent Application No. EP13824744.0 dated Feb. 26, 2016.
First Office Action for Chinese Patent Application No. 201380049844.9 dated Dec. 28, 2015 (w/translation).
Fu et al. Multiplex detection and SNP genotyping in a single fluorescence channel. PLoS One 7(1):Article No. e30340 (Jan. 2012).
Han, et al., Quantum-dot-tagged microbeads for multiplexed optical coding of biomolecules. Nature Biotechnology 19.99 (Jul. 2001): 631-635.
Haustein et al. Fluorescence correlation spectroscopy: novel variations of an established technique. Ann Rev Biophys Biomol Struct 36:151-69 (2007).
PCT/US19/40392 International Search Report and Written Opinion dated Nov. 6, 2019.
PCT/US2013/053512 International Search Report and Written Opinion dated Oct. 16, 2013.
Rajagopal et al. Supercolor Coding Methods for Large-Scale Multiplexing of Biochemical Assays. Analytical Chemistry 85:7629-7636 (2013).
Second Office Action for Chinese Patent Application No. 201380049844.9 dated Sep. 19, 2016 (w/translation).
ThermoFisher Scientific Fluorescence SpectraViewer. Retrieved from http://www.thermofisher.com/us/en/home/life-science/cell-analysis/labeling-chemistry/fluorescence-spectraviewer.html on Sep. 25, 2015.
U.S. Appl. No. 13/958,479 Office Action dated Mar. 1, 2016.
U.S. Appl. No. 15/892,245 First Action Interview—Office Action mailed Jul. 19, 2018.
U.S. Appl. No. 16/128,343 Office Action dated Oct. 15, 2019.
U.S. Appl. No. 15/914,356 Office Action dated Jul. 22, 2019.
U.S. Appl. No. 15/914,356 Office Action dated Mar. 8, 2019.
Vogelstein, et al., Digital PCR, PNAS Aug. 3, 1999 96 (16) 9236-9241; https://doi.org/10.1073/pnas.96.16.9236.
Zhao et al. Comprehensive Algorithm for Quantitative Real-Time Polymerase Chain Reaction. Journal of Computational Biology 12(8):1047-1064 (2005).
Arya, et al., Basic principles of real-time quantitative PCR, 2005, Expert Rev. Mol. Diagn., 5(2), p. 209-219.
Co-pending U.S. Appl. No. 16/864,744, inventors Kartalovemil; P. et al., filed May 1, 2020.
European Patent Application No. 17776626 Office Action dated Oct. 18, 2019.
International Search Report and Written Opinion dated Nov. 21, 2019 for PCT/US2019/050050.
Loftis et al., Principles of real-time PCR. Veterinary PCR Diagnostics pp. 3-17 (2012).
Logan, et al., An Overview of real-time PCR platforms. 2004, In Real-time PCR: An essential guide, p. 13-30.
Morgan et al., A commercial line probe assay for the rapid detection of rifampicin resistance in *Mycobacterium tuberculosis*: a systematic review and meta-analysis. BMC Infectious Diseases. 5:62 doi:10.1186/1471-2334-5-62 (2005).
Navarro et al., Real-time PCR detection chemistry. Clin Chim Acta. 439:231-250 (2015).
PCT/US2018/039846 International Preliminary Report on Patentability dated Dec. 31, 2019.
PCT/US2018/055927 International Preliminary Report on Patentability dated Apr. 21, 2020.
PCT/US2019/019906 International Preliminary Report on Patentability Sep. 1, 2020.
PCT/US2019/019906 International Search Report and Written Opinion dated May 6, 2019.
PCT/US2019/027751 International Preliminary Report on Patentability dated Oct. 20, 2020.
PCT/US2019/027751 International Search Report and Written Opinion dated Jun. 26, 2019.
PCT/US2019/035129 Invitation to Pay Additional Fees dated Aug. 19, 2019.
PCT/US2019/041239 International Search Report and Written Opinion dated Sep. 30, 2019.
Pierce, et al. Linear-After-The-Exponential (LATE)-PCR: primer design criteria for high yields of specific single-stranded DNA and improved real-time detection. Proc Natl Acad Sci U S A. Jun. 14, 2005;102(24):8609-14. Epub Jun. 3, 2005.
Rajagopal et al., Significant Expansion of Real-Time PCR Multiplexing with Traditional Chemistries using Amplitude Modulation. Scientific Reports. 9(1): 1053 (2019).
Rickert et al., "Multiplexed Real-Time PCR Using Universal Reporters," Clin. Chem., 50(9):1680-1683, 2004.
U.S. Appl. No. 15/892,245 Office Action dated Dec. 31, 2018.
U.S. Appl. No. 16/020,673 Non-Final Office Action dated Nov. 27, 2020.
U.S. Appl. No. 15/892,245 Office Action dated Dec. 11, 2019.
U.S. Appl. No. 15/892,245 Office Action dated Jun. 17, 2019.
U.S. Appl. No. 15/701,014 Office Action dated Jan. 24, 2020.
Belák et al., Novel and rapid technologies for the early diagnosis and molecular epidemiology of viral diseases (Ed. Odongo et al.). Sustainable Improvement of Animal Production and Health, FAO of the UN, Rome. pp. 295-303 (2010).
Biosearchtm Technologies, Spectral Overlay Tool for multiplexed qPCR. LGC Biosearch Technologies. 2pgs. Retrieved on Oct. 11, 2023 from https://www.biosearchtech.com/qpcr-multiplex-spectral-overlay-tool (2023).
Elnifro et al., Multiplex PCR: optimization and application in diagnostic virology. Clin Microbiol Rev. 13(4):559-570 (2000).
Faltin et al., Current methods for fluorescence-based universal sequence-dependent detection of nucleic acids in homogenous assays and clinical applications. Clin Chem. 59(11):1567-1582 (2013).
Faltin et al., Mediator probe PCR: a novel approach for detection of real-time PCR based on label-free primary probes and standardized secondary universal fluorogenic reporters. Clin Chem. 58(11):1546-1556 (2012).
Gentile et al., Verification of monoplex and multiplex linear-after-the-exponential PCR gene-specific sepsis assays using clinical isolates. J Appl Microbiol. 114(2):586-594 (2013).
Markoulatos et al., Multiplex polymerase chain reaction: a practical approach. J Clin Lab Anal. 16(1):47-51 (2002).
Murakami et al., Specific detection and quantitation of SCC antigen 1 and SCC antigen 2 mRNAs by fluorescence-based asymmetric semi-nested reverse transcription PCR. Tumour Biol. 21(4):224-234 (2000).
Ongagna-Yhombi et al., Improved assay to detect Plasmodium falciparum using an uninterrupted, semi-nested PCR and quantitative lateral flow analysis. Malar J. 12:74, pp. 1-8 (2013).
Putignani et al., Investigation of Toxoplasma gondii presence in farmed shellfish by nested-PCR and real-time PCR fluorescent amplicon generation assay (FLAG). Exp Parasitol. 127(2):409-417 (2011).
Sanchez et al., Linear-after-the-exponential (LATE)-PCR: an advanced method of asymmetric PCR and its uses in quantitative real-time analysis. Proc Natl Acad Sci USA. 101(7):1933-1938 (2004).
Sharath Chandra G, et al. Modified competing polymerase chain reaction primer for single tube quantitative PCR. Anal Biochem. 427(2):175-177 (2012).
Wittwer et al., Rapid polymerase chain reaction and melting analysis. The PCR Revolution: Basic Technologies and Applications (Ed. S. Bustin). Ch. 4: 48-69 (2010).
Wittwer et al., Real-time multiplex PCR assays. Methods. 25(4):430-442 (2001).
European Application No. 18824489 Search Report dated Mar. 9, 2021.
Myers et al., A Handheld Point-of-Care Genomic Diagnostic System. PLoS One 8(8): e70266; pp. 1-9 (2013).

(56) References Cited

OTHER PUBLICATIONS

PCT/US2019/035129 International Search Report and Written Opinion dated Nov. 1, 2019.
PCT/US2019/040392 International Preliminary Report on Patentability dated Jan. 5, 2021.
PCT/US2021/027127 International Search Report and Written Opinion dated Aug. 3, 2021.
Robin, Jerome D. et al. Comparison of DNA Quantification Methods for Next Generation Sequencing, Scientific Reports, vol. 6, Article No. 24067, pp. 1-10 (Apr. 6, 2016).
U.S. Appl. No. 16/020,673 Final Office Action dated Sep. 2, 2021.
U.S. Appl. No. 16/051,736 Office Action dated Aug. 21, 2020.
Whale, et al. Fundamentals of multiplexing with digital PCR. Biomolecular Detection and Quantification 10 (2016): 15-23.
Zhong, et al. Multiplex digital PCR: breaking the one target per color barrier of quantitative PCR. Lab Chip. Jul. 7, 2011;11(13):2167-74. doi: 10.1039/c1lc20126c. Epub May 17, 2011.

\* cited by examiner

FORMULATIONS AND SIGNAL ENCODING AND DECODING METHODS FOR MASSIVELY MULTIPLEXED BIOCHEMICAL ASSAYS

CROSS-REFERENCE

This application claims priority to U.S. Provisional Patent Application No. 62/693,777, filed on Jul. 3, 2018, which application is incorporated herein by reference in its entirety.

BACKGROUND

Non-degenerate coding schemes can be used to detect multiple analytes in a single signal measurement. However, current multiplexing technologies which rely on fully non-degenerate coding schemes may be limited by technical restrictions such as reagent concentration requirements and signal detection capabilities.

SUMMARY

Disclosed herein are methods and compositions for unambiguous detection of multiple analytes. In some cases, multiple analytes may be detected using a single optical channel, without the need for a fully non-degenerate coding scheme.

In some aspects, provided herein is a method of detecting the presence or absence of at least three polynucleotide analytes in a sample, in any combination of presence or absence, the method comprising: (a) contacting a first subset of the sample with a first plurality of hybridization probes to generate a first cumulative signal measurement comprising one or more signals generated from the first plurality of hybridization probes, wherein the first cumulative signal measurement fails to non-degenerately identify the presence or absence of any combination of the at least three polynucleotide analytes; (b) contacting one or more additional subsets of the sample with one or more additional pluralities of hybridization probes to generate one or more additional cumulative signal measurements each comprising one or more additional signals generated from the one or more additional plurality of hybridization probes, wherein each of the one or more additional cumulative signal measurements fails to non-degenerately identify the presence or absence of any combination of the at least three polynucleotide analytes; and (c) comparing the first cumulative signal measurement to the one or more additional cumulative signal measurements, wherein the comparing uniquely identifies any combination of the polynucleotide analytes in the sample, thereby detecting the presence or absence of the least three polynucleotide analytes in the sample, in any combination of presence or absence. In some embodiments, the first subset and the one or more additional subsets are each in the same solution volume. In some embodiments, the first subset and the one or more additional subsets are each in different solution volumes. In some embodiments, the first subset and the one or more additional subsets are each provided in a plurality of partitions. In some embodiments, the first subset and the one or more additional subsets are each provided in a well. In some embodiments, the number of unique hybridization probes in the first plurality of hybridization probes is less than or equal to the number of unique polynucleotide analytes in the at least three polynucleotide analytes. In some embodiments, the number of unique hybridization probes in each of the one or more additional plurality of hybridization probes is less than or equal to the number of unique polynucleotide analytes in the at least three polynucleotide analytes. In some embodiments, the first plurality of hybridization probes and the one or more additional plurality of hybridization probes are oligonucleotide probes. In some embodiments, the first plurality of hybridization probes and the one or more additional plurality of hybridization probes each comprise a fluorophore. In some embodiments, generating the first cumulative signal measurement and the one or more additional cumulative signal measurements comprises exciting the fluorophores and detecting the signals generated from each fluorophore. In some embodiments, each hybridization probe of the first plurality of hybridization probes and the one or more additional plurality of hybridization probes comprises a fluorophore capable of being detected in the same optical channel. In some embodiments, each hybridization probe of the first plurality of hybridization probes and the one or more additional plurality of hybridization probes comprises the same fluorophore. In some embodiments, each hybridization probe of the first plurality of hybridization probes and the one or more additional plurality of hybridization probes is provided at a different concentration. In some embodiments, the at least three polynucleotide analytes are at least seven polynucleotide analytes. In some embodiments, generating the first cumulative signal measurement and the one or more additional cumulative signal measurements comprises polymerase chain reaction (PCR). In some embodiments, first cumulative signal measurement and the one or more additional cumulative signal measurements comprise a signal intensity. In some embodiments, the first cumulative signal measurement comprises an ambiguity, and wherein the one or more additional cumulative signal measurements resolves the ambiguity. In some embodiments, the method does not require any step of immobilization of the polynucleotide analytes, microscopy, flow cytometry, physical separation of the polynucleotide analytes, mass spectrometry, or melting curve analysis. In some embodiments, each of the first plurality of hybridization probes and the one or more additional pluralities of hybridization probes corresponds to one of the at least three polynucleotide analytes. In some embodiments, each of the first plurality of hybridization probes and the one or more additional pluralities of hybridization probes has complementarity to one of the at least three polynucleotide analytes. In some embodiments, the PCR is digital PCR. In some embodiments, the PCR is quantitative PCR.

In some aspects, provided herein is a method of detecting the presence or absence of at least three polynucleotide analytes in a sample, in any combination of presence or absence, the method comprising: (a) providing a first and second sample solution volume, each comprising, or potentially comprising, the at least three polynucleotide analytes; (b) contacting the first sample solution volume with a first plurality of hybridization probes, each corresponding to one of the polynucleotide analytes, to generate a first cumulative signal measurement comprising one or more signals generated from the first plurality of hybridization probes, wherein the first cumulative signal measurement fails to non-degenerately identify the presence or absence of any combination of the at least three polynucleotide analytes; (c) contacting the second sample solution volume with a second plurality of hybridization probes, each corresponding to one of the polynucleotide analytes, to generate a second cumulative signal measurement comprising one or more signals generated from the second plurality of hybridization probes, wherein the second cumulative signal measurement fails to non-degenerately identify the presence or absence of any combination of the at least three polynucleotide analytes; and (d) comparing the first cumulative signal measurement to the second cumulative signal measurement, wherein the comparing uniquely identifies any combination of polynucleotide analytes in the sample, thereby detecting the presence or absence of at least three polynucleotide analytes in a sample, in any combination of presence or absence. In some embodiments, the first and second sample solution volume are derived from the sample. In some embodiments, the number of unique hybridization probes in the first plurality of hybridization probes is less than or equal to the number of unique polynucleotide analytes in the at least three polynucleotide analytes. In some embodiments, the number of unique hybridization probes in the first plurality of hybridization probes is equal to the number of unique polynucleotide analytes in the at least three polynucleotide analytes. In some embodiments, the number of unique hybridization probes in the second plurality of hybridization probes is less than or equal to the number of unique polynucleotide analytes in the at least three polynucleotide analytes. In some embodiments, the number of unique hybridization probes in the second plurality of hybridization probes is less than the number of unique polynucleotide analytes in the at least three polynucleotide analytes. In some embodiments, the first plurality of hybridization probes are oligonucleotide probes. In some embodiments, the first plurality of hybridization probes each comprise a fluorophore. In some embodiments, each hybridization probe of the first plurality of hybridization probes comprises a fluorophore capable of being detected in the same optical channel. In some embodiments, each hybridization probe of the first plurality of hybridization probes comprises the same fluorophore. In some embodiments, each hybridization probe of the first plurality of hybridization probes is provided at a different concentration. In some embodiments, generating the first cumulative signal measurement comprises exciting the fluorophores and detecting the signals generated from each fluorophore. In some embodiments, the second plurality of hybridization probes are oligonucleotide probes. In some embodiments, the second plurality of hybridization probes each comprise a fluorophore. In some embodiments, each hybridization probe of the second plurality of hybridization probes comprises a fluorophore capable of being detected in the same optical channel. In some embodiments, each hybridization probe of the first plurality of hybridization probes comprises the same fluorophore. In some embodiments, each hybridization probe of the second plurality of hybridization probes is provided at a different concentration. In some embodiments, generating the second cumulative signal measurement comprises exciting the fluorophores and detecting the signals generated from each fluorophore. In some embodiments, the at least three polynucleotide analytes are at least five polynucleotide analytes. In some embodiments, the at least three polynucleotide analytes are at least seven polynucleotide analytes. In some embodiments, the first plurality of hybridization probes and the second plurality of hybridization probes are the same. In some embodiments, the first plurality of hybridization probes and the second plurality of hybridization probes are different. In some embodiments, the first plurality of hybridization probes comprises (i) a first hybridization probe corresponding to a first polynucleotide analyte of the at least three polynucleotide analytes and (ii) a second hybridization probe corresponding to a second polynucleotide analyte of the at least three polynucleotide analytes, and wherein the second plurality of hybridization probes comprises (1) a third hybridization probe corresponding to the first polynucleotide analyte of the at least three polynucleotide analytes and (2) a fourth hybridization probe corresponding to a third polynucleotide analyte. In some embodiments, the third hybridization probe and the first hybridization probe are provided at different concentrations. In some embodiments, the first cumulative signal measurement comprises an ambiguity, and wherein the second cumulative signal measurement resolves the ambiguity of the first cumulative signal measurement. In some embodiments, the ambiguity is a signal that fails to unambiguously identify a single combination of polynucleotide analytes of the at least three polynucleotide analytes. In some embodiments, the method does not require any step of immobilization of the polynucleotide analytes, microscopy, flow cytometry, physical separation of the polynucleotide analytes, mass spectrometry, or melting curve analysis.

In some aspects, provided herein is a method of detecting the presence or absence of a plurality of polynucleotide analytes in a sample, in any combination of presence or absence, the method comprising: (a) providing a first and second sample solution volume, each comprising, or potentially comprising, the plurality of polynucleotide analytes; (b) contacting the first sample solution volume with a first plurality of hybridization probes to generate a first cumulative signal measurement that fails to non-degenerately indicate the presence or absence of any combination of the plurality of analytes; (c) contacting the second sample solution volume with a second plurality of hybridization probes to generate a second cumulative signal measurement that fails to non-degenerately indicate the presence or absence of any combination of the plurality of analytes; and (d) comparing the first cumulative signal measurement to the second cumulative signal measurement, thereby non-degenerately indicating the presence or absence of the plurality of analytes, in any combination of presence or absence. In some aspects, provided herein is a method of detecting the presence or absence of a plurality of polynucleotide analytes in a sample solution volume, in any combination of presence or absence, the method comprising: (a) contacting the sample solution volume with a first plurality of hybridization probes to generate a first cumulative signal measurement that fails to non-degenerately indicate the presence or absence of any combination of the plurality of analytes, wherein the first plurality of hybridization probes are attached to fluorophores capable of being detected in a first signal channel; (b) contacting the sample solution volume with a second plurality of hybridization probes to generate a second cumulative signal measurement that fails to non-degenerately indicate the presence or absence of any combination of the plurality of analytes wherein the second plurality of hybridization probes are attached to fluorophores capable of being detected in a second signal channel; and (c) comparing the first cumulative signal measurement to the second cumulative signal measurement, thereby non-degenerately indicating the presence or absence of the plurality of analytes, in any combination of presence or absence.

In some embodiments, the method does not require any step of immobilization of the polynucleotide analytes, microscopy, flow cytometry, mass spectrometry, or melting curve analysis. In some embodiments, the plurality of polynucleotide analytes comprises at least three polynucleotide analytes. In some embodiments, the plurality of polynucleotide analytes comprises at least seven polynucleotide analytes. In some embodiments, the number of unique hybridization probes in the first plurality of hybridization probes is less than or equal to the number of unique polynucleotide analytes in the plurality of polynucleotide analytes. In some embodiments, the number of unique hybridization probes in the first plurality of hybridization probes is equal to the number of unique polynucleotide analytes in the plurality of polynucleotide analytes. In some embodiments, the number of unique hybridization probes in the second plurality of hybridization probes is less than or equal to the number of unique polynucleotide analytes in the plurality of polynucleotide analytes. In some embodiments, the number of unique hybridization probes in the second plurality of hybridization probes is less than the number of unique polynucleotide analytes in the plurality of polynucleotide analytes. In some embodiments, the first cumulative signal measurement is detected in a first color channel, and the second cumulative signal measurement is detected in a second color channel. In some embodiments, one or more of the first plurality of hybridization probes corresponds to one or more of the plurality of polynucleotide analytes. In some embodiments, one or more of the second plurality of hybridization probes corresponds to one or more of the plurality of polynucleotide analytes. In some embodiments, one or more of the first plurality of hybridization probes corresponds to a region of an oligonucleotide which corresponds to one or more of the plurality of polynucleotide analytes. In some embodiments, one or more of the second plurality of hybridization probes corresponds to a region of an oligonucleotide which corresponds to one or more of the plurality of polynucleotide analytes.

In some aspects, provided herein is a method of detecting the presence or absence of a plurality of polynucleotide analytes in a sample solution volume, the method comprising: (a) providing the sample solution volume comprising, or potentially comprising, the plurality of polynucleotide analytes; (b) contacting the sample solution volume with a plurality of hybridization probes and exciting the hybridization probes to generate a cumulative signal measurement if one or more of the plurality of polynucleotide analytes is present in the sample solution volume, wherein the cumulative signal measurement comprises an ambiguity; (c) receiving a set of information regarding the polynucleotide analytes; and (d) comparing the cumulative signal measurement to the set of information, wherein the results of the comparing resolve the ambiguity, thereby detecting the presence or absence of the plurality of polynucleotide analytes. In some embodiments, the method does not require any step of immobilization of the polynucleotide analytes, microscopy, flow cytometry, physical separation of the polynucleotide analytes, mass spectrometry, or melting curve analysis. In some embodiments, the plurality of polynucleotide analytes comprises at least three polynucleotide analytes. In some embodiments, the plurality of polynucleotide analytes comprises at least seven polynucleotide analytes. In some embodiments, the number of unique hybridization probes in the plurality of hybridization probes is less than or equal to the number of unique polynucleotide analytes in the plurality of polynucleotide analytes. In some embodiments, the number of unique hybridization probes in the first plurality of hybridization probes is equal to the number of unique polynucleotide analytes in the plurality of polynucleotide analytes. In some embodiments, the number of unique hybridization probes in the first plurality of hybridization probes is less than the number of unique polynucleotide analytes in the plurality of polynucleotide analytes. In some embodiments, each hybridization probe comprises at least one fluorophore. In some embodiments, the at least one fluorophore is selected from three, four, five, or six fluorophores. In some embodiments, the set of information comprises an additional cumulative signal measurement generated prior to (a), wherein comparing the cumulative signal measurement to the additional cumulative signal measurement resolves the ambiguity. In some embodiments, the set of information comprises a statistical table, wherein comparing the data from the statistical table to the cumulative signal measurement resolves the ambiguity. In some embodiments, the set of information comprises a desired clinical outcome. In some embodiments, the desired clinical outcome is identification of a treatment strategy for a patient. In some embodiments, the patient is suspected of being infected with a bacterial agent or a viral agent.

In some aspects, provided herein is an assay comprising: (a) a first reaction that fails to non-degenerately detect the presence or absence of any combination of the plurality of analytes; and (b) a second reaction that fails to non-degenerately detect the presence or absence of any combination of the plurality of analytes; wherein the results of the first reaction and second reaction unambiguously detect the presence or absence of each of at least three analytes without immobilization of the analytes, mass spectrometry, microscopy, flow cytometry, or melting curve analysis. In some embodiments, the first reaction and the second reaction are performed in the same sample solution volume. In some embodiments, the first reaction is performed in a first sample solution volume and the second reaction is performed in a second sample solution volume. In some embodiments, the first sample solution volume and the second sample solution volume each comprise, or potentially comprise, the at least three analytes. In some embodiments, the at least three analytes are polynucleotide analytes. In some embodiments, the at least three analytes are at least five analytes. In some embodiments, the at least three analytes are at least seven analytes. In some embodiments, the first reaction comprises an ambiguity, and wherein the second reaction resolves the ambiguity. In some embodiments, the ambiguity is a signal that fails to unambiguously identify a single combination of polynucleotide analytes of the at least three polynucleotide analytes. In some embodiments, the first reaction and the second reaction each comprise a polymerase chain reaction. In some embodiments, the first reaction comprises generating a first cumulative signal measurement from one or more signals. In some embodiments, the one or more signals are generated from one or more hybridization probes. In some embodiments, the second reaction comprises generating a second cumulative signal measurement from one or more signals. In some embodiments, the one or more signals are generated from one or more hybridization probes. In some embodiments, the first reaction comprises generating one or more first signals detected in a first signal channel, and wherein the second reaction comprises generating one or more second signals detected in a second signal channel.

In some aspects, provided herein is a composition for detecting a plurality of polynucleotide analytes comprising a plurality of hybridization probes each corresponding to one of the plurality of polynucleotide analytes and comprising at least one fluorophore, wherein each hybridization probe, when excited and when contacted with its corresponding polynucleotide analyte, generates a cumulative intensity signal, and wherein a cumulative signal measurement generated from the cumulative intensity signal from the plurality of hybridization probes forms a Sidon sequence. In some embodiments, the at least one fluorophore is selected from three, four, five, or six fluorophores. In some embodiments, the plurality of hybridization probes comprises at least seven unique hybridization probes. In some embodiments, the composition comprises a first hybridization probe at a concentration of at least 1×, a second hybridization probe at a concentration of at least 4×, a third hybridization probe at a concentration of at least 9×, a fourth hybridization probe at a concentration of at least 15×, a fifth hybridization probe at a concentration of at least 22×, a sixth hybridization probe at a concentration of at least 32×, and a seventh hybridization probe at a concentration of at least 34×.

In some aspects, provided herein is a method of non-degenerately detecting the presence or absence of a plurality of polynucleotide analytes, in any combination of presence or absence, comprising: (a) providing a sample solution volume comprising, or potentially comprising, at least one of the plurality of polynucleotide analytes; (b) providing a plurality of hybridization probes, each comprising at least one fluorophore, wherein each hybridization probe generates a cumulative intensity signal, and wherein a cumulative signal measurement generated from the cumulative intensity signals from the plurality of hybridization probes forms a Sidon sequence; and (c) contacting the sample solution volume with the plurality of hybridization probes to generate the cumulative signal measurement, thereby non-degenerately detecting the presence or absence of the plurality of analytes, in any combination of presence or absence. In some embodiments, the method does not require any step of immobilization of the polynucleotide analytes, physical separation of the polynucleotide analytes, mass spectrometry, or melting curve analysis. In some embodiments, the plurality of polynucleotide analytes is at least seven polynucleotide analytes. In some embodiments, one or more of the plurality of hybridization probes binds to one or more of the plurality of polynucleotide analytes. In some embodiments, one or more of the plurality of hybridization probes binds to a region of an oligonucleotide which corresponds to one or more of the plurality of polynucleotide analytes.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows a schematic of a first reaction comprising a degeneracy. FIG. 1B shows a schematic of a second reaction capable of resolving the degeneracy from the first reaction. FIG. 1C shows a comparison of the first and second reactions.

FIG. 10A shows an example where only a single target (Inf A H1) is present. FIG. 10B shows an example where two targets (Inf A H1 and Inf A H3) are present.

DETAILED DESCRIPTION

Figure 1A:
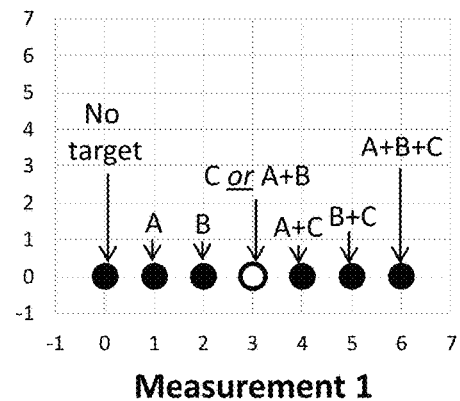
FIGS. 1A-1C show a schematic of an example assay of the present disclosure comprising two measurements, capable of non-degenerately measuring three analytes from a sample.

Polymerase Chain Reaction (PCR) is a method of exponential amplification of specific target nucleic acid in a reaction mix with a nucleic acid polymerase and primers. Primers are short single stranded oligonucleotides which are complementary to the 3' sequences of the positive and negative strand of the target sequence. The reaction mix is cycled in repeated heating and cooling steps. The heating cycle denatures or splits a double stranded nucleic acid target into single stranded templates. In the cooling cycle, the primers bind to complementary sequence on the template. After the template is primed the nucleic acid polymerase creates a copy of the original template. Repeated cycling exponentially amplifies the target 2 fold with each cycle leading to approximately a billion-fold increase of the target sequence in 30 cycles (Saiki et al 1988).

Digital PCR is a process of partitioning a sample containing one or more targets into a plurality of partitions (e.g., wells, droplets, etc.), performing a PCR reaction in each partition, and recording the fluorescence generated by, for example, a target-specific reporter probe. This is generally performed on a digital PCR instrument that measures the fluorescence from each partition in an optical channel through one or more excitation/emission filter sets.

Frequently, the target-specific nucleic acid probe is a short oligonucleotide complementary to one strand of the amplified target. The probe lacks a 3' hydroxyl and therefore is not extendable by the DNA polymerase. TaqMan (ThermoFisher Scientific) chemistry is a common reporter probe method used for multiplex Real-Time PCR (Holland et al. 1991). The TaqMan oligonucleotide probe is covalently modified with a fluorophore and a quenching tag (i.e., quencher). In this configuration the fluorescence generated by the fluorophore is quenched and is not detected by the real time PCR instrument. When the target of interest is present, the probe oligonucleotide base pairs with the amplified target. While bound, it is digested by the 5' to 3' exonuclease activity of the Taq polymerase thereby physically separating the fluorophore from the quencher and liberating signal for detection by the real time PCR instrument.

Multiplex analysis of multiple analytes in a single measurement may be performed by encoding each analyte to a unique intensity value. For example, for detection of multiple polynucleotide analytes in a sample using a single measurement, hybridization probes may be provided at varying concentrations, such that the intensity of each signal generated from the probes, both individually and in combination, is unique. Table 1 shows an example reaction mixture, formulated to uniquely detect any combination of three nucleic acids in a single fluorometric polymerase chain reaction (PCR) measurement.

TABLE 1

|  | Fluorescent Probe | Forward Primer | Reverse Primer |
| --- | --- | --- | --- |
| Target A | 300 nM | 1200 nM | 1200 nM |
| Target B | 600 nM | 1200 nM | 1200 nM |
| Target C | 1200 nM | 1200 nM | 1200 nM |

In this case, the final intensity of the output of the fluorescence measurement at the end of the PCR reaction is a linear combination of the input probe concentration such that all probe gets exhausted during a reaction for which a target is present, and every possible combination of targets results in a unique final fluorescent intensity. In this case, the intensity of the signal generated can be directly correlated with the targets that are present in the sample, as shown in Table 2.

TABLE 2

| Fluorescent Intensity (normalized) | Targets present in sample |
| --- | --- |
| 7x | A, B, and C |
| 6x | B and C |
| 5x | A and C |
| 4x | C |
| 3x | A and B |
| 2x | B |
| 1x | A |

Use of such a fully non-degenerate method for multiplex analysis may require sufficient assay conditions for generating and measuring each signal intensity level. For example, probe concentrations may need to be provided such that they generate sufficiently distinct intensity levels at every possible combination, and signal detection methods must be capable of detecting each unique intensity level. Recognized herein is a need for methods and compositions for unambiguous detection of multiple analytes from a sample that minimize the conditions necessary for such detection (e.g., reagent concentrations, measurement capabilities, etc.).

Definitions

The term "complementarity," or "complementary," as used herein, can refer to a property of a nucleic acid or the region of a nucleic acid wherein the nucleic acid is capable of binding, annealing, or otherwise attaching to another nucleic acid under a given set of conditions. A region of a nucleic acid which has complementarity to a region of another nucleic acid can comprise nucleotides which are complementary to those on the other nucleic acid. Complementarity may be of varying degrees. For example, a region of a nucleic acid can have between about 50% and about 100%, between about 60% and about 100%, between about 70% and about 100%, between about 80% and about 100%, between about 90% and about 100%, between about 95% and about 100%, between about 99% and about 100%, or about 100% complementarity to a region of another nucleic acid. Degrees of complementarity can describe the portion of a nucleic acid which is capable of attaching to another nucleic acid under appropriate conditions. Degrees of complementarity can describe the amount of a nucleic acid which comprises nucleotides which are the complement of those on another nucleic acid. A nucleic acid with complementarity can be a double-stranded nucleic acid. A nucleic acid with complementarity can be a single-stranded nucleic acid. A single-stranded nucleic acid which is complementary to another single-stranded nucleic acid can bind to a region of another single-stranded nucleic acid under appropriate conditions. Appropriate conditions for binding of one complementary nucleic acid to another can include appropriate buffer conditions and appropriate temperature conditions. Appropriate buffer conditions can include appropriate salt concentrations, such as concentrations of sodium salts, magnesium salts, or potassium salts. Appropriate temperature conditions can include an annealing temperature which is appropriate for binding of one nucleic acid to another. While a nucleic acid with complementarity to another nucleic acid may attach to another nucleic acid under appropriate conditions, the same nucleic acid may not bind under inappropriate conditions, such as inappropriate salt concentrations or temperature conditions.

The term "homologous" or "homology", as used herein, can refer to a property of a nucleic acid or the region of a nucleic acid wherein the nucleic acid comprises nucleotides which are identical to those comprised in another nucleic acid. A nucleic acid which is homologous to another nucleic acid can comprise one or more nucleotides which are identical to those on the other nucleic acid. Homology may be of varying degrees, depending on the number of nucleotides which are identical. A region of a nucleic acid which is homologous to a region of another nucleic acid may have a certain degree of homology. For example, a region of a nucleic acid can have between about 50% and about 100%, between about 60% and about 100%, between about 70% and about 100%, between about 80% and about 100%, between about 90% and about 100%, between about 95% and about 100%, between about 99% and about 100%, or about 100% homology to a region of another nucleic acid.

Overview

The present disclosure provides methods and compositions for highly multiplexed biochemical assays useful in detecting multiple analytes from a sample. The assays of the present disclosure may be used to non-degenerately detect three or more analytes from a sample. The disclosed methods and compositions may require a lower number of signal intensity levels relative to existing multiplex assays.

In one example, three or more nucleic acid analytes from a biological sample may be detected in a single color channel by qPCR. Fluorescent probes and appropriate primers may be provided as shown in Table 3.

TABLE 3

|  | Fluorescent Probe | Forward Primer | Reverse Primer |
| --- | --- | --- | --- |
| Target A | 300 nM | 1200 nM | 1200 nM |
| Target B | 600 nM | 1200 nM | 1200 nM |
| Target C | 900 nM | 1200 nM | 1200 nM |

In this case, only six fluorescence intensity levels are required to measure any combination of analytes, as shown in Table 4. However, the measurement comprises a degeneracy at the 3x fluorescent intensity level. In this example, a measurement of a 3x intensity level will indicate either the presence of both Target A and Target B, or the presence of Target C. Without additional information, the results cannot be disambiguated.

TABLE 4

| Fluorescent Intensity (normalized) | Targets present |
|---|---|
| 6x | A, B, and C |
| 5x | B and C |
| 4x | A and C |
| 3x | (A and B) or C |
| 2x | B |
| 1x | A |
| 0x | None |

As described herein, additional information regarding the target analytes can be obtained and compared with the results of the measurement, thereby resolving the ambiguity. The additional information may be, for example, a statistical table, a desired clinical outcome, or the results of an additional measurement.

Assays

In some aspects, the present disclosure provides assays for unambiguously detecting the presence or absence of multiple analytes in a sample. The disclosed assays may detect the presence or absence of each of at least three analytes, in any combination of presence or absence, without the use of one or more of: immobilization of the analytes, mass spectrometry, microscopy, flow cytometry, or melting curve analysis. Analyte detection may be accomplished by the use of two or more reactions. For example, an assay for measuring a plurality of analytes may comprise a first reaction and a second reaction. Both a first and second reaction may, alone, fail to non-degenerately detect the presence or absence of any combination of analytes. The results of the first and second reactions may together unambiguously detect the presence or absence of each of the analytes.

Any number of analytes may be detected using assays of the present disclosure. In some cases, an assay may unambiguously detect at least 3, 4, 5, 6, 7, 8, 9, 10, 11, 12, 13, 14, 15, 20, 30, 40, 50 analytes, or more. In some cases, an assay may unambiguously detect at most 50, 40, 30, 20, 15, 14, 13, 12, 11, 10, 9, 8, 7, 6, 5, 4, or 3 analytes. An assay may comprise any number of reactions, where the results of the reactions together identify a plurality of analytes, in any combination of presence or absence. An assay may comprise 2, 3, 4, 5, 6, 7, 8, 9, 10 reactions, or more. Each reaction may be individually incapable of non-degenerately detecting the presence or absence of any combination of analytes. However, the results of each reaction together may unambiguously detect the presence or absence of each of the analytes.

Reactions may be performed in the same sample solution volume. For example, a first reaction may generate a fluorescent signal in a first color channel, while a second reaction may generate a fluorescent signal in a second color channel, thereby generating two measurements for comparison. Alternatively, reactions may be performed in different sample solution volumes. For example, a first reaction may be performed in a first sample solution volume and generate a fluorescent signal in a given color channel, and a second reaction may be performed in a second sample solution volume and generate a fluorescent signal in the same color channel or a different color channel, thereby generating two measurements for comparison.

A reaction may be performed in a single partition (e.g., a well). A reaction may be performed in a plurality of partitions (e.g., a plurality of droplets). A reaction may comprise polymerase chain reaction (PCR). A reaction may comprise, for example, quantitative PCR (qPCR), digital PCR (dPCR), or droplet digital PCR (ddPCR). In some cases, a single reaction comprises a single PCR reaction (e.g., qPCR, dPCR, ddPCR). The results of two or more reactions (e.g., PCR reactions) may be compared, thereby unambiguously detecting the presence or absence of any combination of a plurality of analytes.

A reaction may comprise generating a cumulative signal measurement. Assays of the present disclosure may comprise comparing two or more cumulative signal measurements to unambiguously detect any combination of analytes in a sample. A cumulative signal measurement may comprise one or more signals generated from one or more probes provided to a sample solution. A cumulative signal measurement may be a signal intensity level which corresponds to the sum of signals generated from multiple hybridization probes. For example, two probes may each bind to an analyte (e.g., a nucleic acid analyte), where each probe generates a signal of a given wavelength at 1× intensity. Measurement of these signals would generate a cumulative signal measurement corresponding to the sum of both signal intensities, namely a 2× signal intensity.

A reaction may comprise an ambiguity. An ambiguity may be a signal that fails to unambiguously identify a single combination of analytes in a sample. For example, a reaction may generate a signal at 2× intensity level. Based on the encoding of the reaction (e.g., the concentration of hybridization probes present in the reaction), a 2× intensity level may correspond to more than one combination of analytes, thereby comprising an ambiguity. An ambiguity may be resolved by performing one or more additional reactions, thereby resolving the ambiguity. For example, a second reaction may generate a 3× signal intensity level, where the presence of both a 2× signal intensity level from a first reaction and a 3× signal intensity level from a second reaction uniquely identifies a given combination of analytes from a sample.

An assay may comprise selecting two or more reactions from a selection of reactions, depending on the information necessary to resolve an ambiguity. For example, a first reaction may comprise an ambiguity at a first signal level and a second signal level. Results corresponding to the first signal level may identify a first additional reaction as necessary to resolve the ambiguity, while results corresponding to the second signal level may identify a second additional reaction as necessary to resolve the ambiguity.

Methods for Analyte Detection

In some aspects, the present disclosure provides methods for detecting the presence or absence of a plurality of analytes in a sample. Analytes may be polynucleotide analytes (e.g., DNA, RNA, etc.). First, a subset of a sample may be contacted with a first plurality of hybridization probes. Each hybridization probe may correspond to a polynucleotide analyte (e.g., may bind to a region of a polynucleotide analyte). A first cumulative signal measurement may be generated comprising one or more signals generated from the first plurality of hybridization probes. The first cumulative signal measurement may fail to non-degenerately identify the presence or absence of any combination of the at least three polynucleotide analytes. Next, one or more additional subsets of the sample may be contacted with one or more additional pluralities of hybridization probes. Each hybridization probe may correspond to a polynucleotide analyte (e.g., may bind to a region of a polynucleotide analyte). One or more additional cumulative signal measurements may be generated, each comprising one or more additional signals generated from the one or more additional pluralities of hybridization probes. The one or more additional cumulative signal measurements may fail to non-degenerately identify the presence or absence of any combination of the at least three polynucleotide analytes. Finally, the first cumulative signal measurement to the one or more additional cumulative signal measurements may be compared. The comparison may uniquely identify any combination of polynucleotide analytes in the sample.

In some aspects, the present disclosure provides methods for detecting the presence or absence of a plurality of analytes in a sample solution volume. Analytes may be polynucleotide analytes (e.g., DNA, RNA, etc.). First, a sample solution volume comprising, or potentially comprising, a plurality of analytes may be provided. The sample solution may be derived from a sample, for example, a sample from a subject. Next, the sample solution volume may be contacted with a plurality of hybridization probes, which may be excited to generate a cumulative signal measurement if one or more of the plurality of analytes is present in the sample solution volume. The cumulative signal measurement may comprise an ambiguity. The ambiguity may be a signal intensity level corresponding to more than one combination of analytes. Next, a set of information regarding the polynucleotide analytes may be received. The set of information may comprise, for example, an additional cumulative signal measurement, a statistical table, or a desired clinical outcome. Finally, the cumulative signal measurement may be compared to the set of information, where the results of the comparing resolve the ambiguity, thereby detecting the presence or absence of analytes.

In some cases, the methods of the present disclosure may be capable of detecting the presence or absence of a plurality of analytes without the use of one or more of: immobilization of the analytes, mass spectrometry, microscopy, flow cytometry, or melting curve analysis. The number of analytes capable of being detected by the disclosed methods may be at least 3, 4, 5, 6, 7, 8, 9, 10, 11, 12, 13, 14, 15, 20, or more, in any combination of presence or absence. The number of unique hybridization probes contacted with a sample solution volume or sample subset may be less than the number of polynucleotide analytes in the sample solution volume. Alternatively, the number of unique hybridization probes contacted with a sample solution volume or sample subset may be equal to the number of polynucleotide analytes in the sample solution volume.

A set of information may comprise a statistical table. A statistical table may comprise information regarding the likelihood of the presence of a given analyte in a sample. A statistical table may be compared to a cumulative signal measurement, thereby resolving an ambiguity. In one example, a cumulative signal measurement generated from a given sample type may correspond to either the presence of Target C alone or of Targets A or B together. A statistical table may comprise information regarding Target A and Target B that demonstrates that there is no possibility that both Target A and Target B will be present together in the given sample type. Therefore, in this example, comparison of the cumulative signal measurement to the statistical table unambiguously identifies the presence of Target C alone.

A set of information may comprise a desired clinical outcome. A desired clinical outcome may be the identification of a treatment strategy for a patient. A desired clinical outcome from an assay may be the identification of a treatment strategy for a patient, where the patient is suspected of being infected with a bacterial agent or viral agent. A cumulative signal measurement may be compared to a clinical outcome, thereby resolving an ambiguity. For example, a cumulative signal measurement may correspond to the presence of any one of a large number of viral genes and the absence of any one of a large number of bacterial genes. The cumulative signal measurement may be compared to a desired clinical outcome, namely the determination of whether a clinician should treat a patient with an antibacterial or antiviral agent. The results of this comparison may unambiguously indicate that the clinician should treat the patient with an antiviral agent.

A set of information may comprise an additional cumulative signal measurement, where the results of the additional cumulative signal measurement are capable of resolving the ambiguity. An additional cumulative signal measurement may comprise a signal that corresponds to a unique combination of polynucleotide analytes. Alternatively, an additional cumulative signal measurement may comprise a signal that corresponds to more than one combination of polynucleotide analytes. Comparing the results of a cumulative signal measurement to an additional cumulative signal measurement may resolve an ambiguity. This may uniquely detect a given combination of polynucleotide analytes from a sample.

Measurement Encoding

In some cases, a degeneracy can be resolved by using the results of one or more additional measurements. For example, a second measurement (e.g., from a second reaction) may be capable of resolving the degeneracy. A second reaction may be performed using a different encoding scheme from the first reaction, such that a comparison of the results of the first and second reactions non-degenerately identifies any combination of analytes. Table 5 shows an example of two reactions each comprising a different coding scheme.

TABLE 5

| Reaction 1 | | | Reaction 2 | | |
| --- | --- | --- | --- | --- | --- |
| Signal Intensity | Probe Encoding | Possible Outputs | Signal Intensity | Probe Encoding | Possible Outputs |
| 6x | | A and B and C | 6x | | A and B |
| 5x | | B and C | 5x | | Invalid state |
| 4x | | A and C | 4x | A | A |
| 3x | C | C or A and B | 3x | | Invalid state |
| 2x | B | B | 2x | B | B |
| 1x | A | A | 1x | | Invalid state |
| 0x | | No targets | 0x | | No targets |

In this case, three targets are encoded for in Reaction 1, while only two of the targets are encoded for in Reaction 2. The result of Reaction 2 can be used to resolve the degeneracy of the "3x" signal intensity level in Reaction 1. This reduces the number of signal intensity levels required to non-degenerately detect any combination of analytes by comparing the results of the two reactions.

Figure 1B:
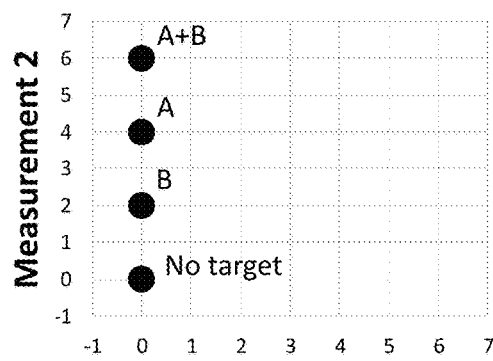
Figure 1C:
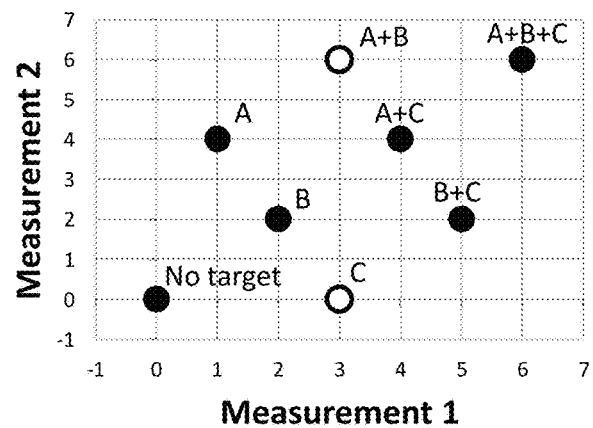
Figure 2:
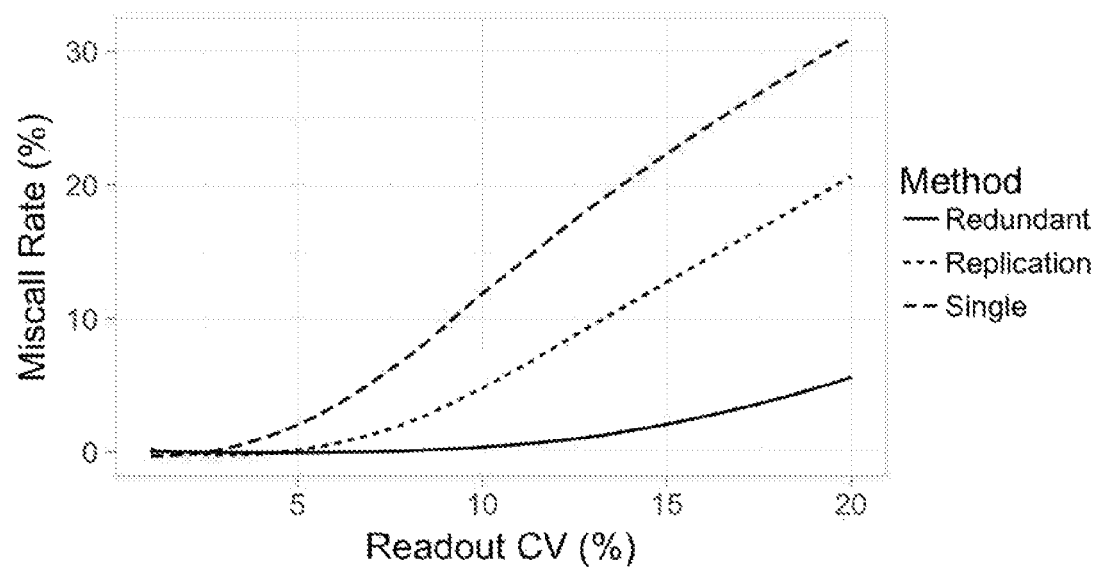
FIG. 2 shows a simulation of expected miscall rates as a function of readout coefficient of variation (CV) for a single measurement, replication of a single measurement, and a redundant measurement.

FIGS. 1A-1C schematically show how two measurements, each of which is individually unable to non-degenerately detect any combination of analytes from a sample, may be compared to unambiguously identify any combination of analytes. FIG. 1A shows the results of a first measurement for each potential combination of three target analytes: A, B, and C. This measurement comprises an ambiguity at the 3x signal intensity level, which may represent either the presence of target C or the presence of targets A and B in combination. FIG. 1B shows the results of a second measurement, which is capable of detecting only two targets analytes: A and B. FIG. 1C shows the results of a comparison of the two measurements, which together can uniquely identify any combination of analytes.

The use of two reactions to non-degenerately identify any combination of analytes, as described herein, may create a sparse code space, which may be useful in error correction and estimation. For example, Table 6 shows a decoding matrix for a two-reaction assay for detecting three analytes based on the reaction scheme in Table 5. Each analyte is identified based on the signal intensity from both Well 1 (reaction 1) and Well 2 (reaction 2). For example, a 2× intensity level in both Well 1 and Well 2 indicates the presence of Target B.

TABLE 6

| Well 1\Well 2 | 0x | 1x | 2x | 3x | 4x | 5x | 6x |
|---|---|---|---|---|---|---|---|
| 0x | None | Invalid | Invalid | C | Invalid | Invalid | Invalid |
| 1x | Invalid | Invalid | Invalid | Invalid | Invalid | Invalid | Invalid |
| 2x | Invalid | Invalid | B | Invalid | Invalid | BC | Invalid |
| 3x | Invalid | Invalid | Invalid | Invalid | Invalid | Invalid | Invalid |
| 4x | Invalid | A | Invalid | Invalid | AC | Invalid | Invalid |
| 5x | Invalid | Invalid | Invalid | Invalid | Invalid | Invalid | Invalid |
| 6x | Invalid | Invalid | Invalid | AB | Invalid | Invalid | ABC |

A decoding matrix for the same two reactions may be designed so as to be resilient to a 1 unit intensity error in any single reaction, as shown in Table 7. In this case, results which would have been identifiable only as errors using a single reaction scheme can be positively identified. For example, a lower or higher intensity level than expected for Target B may be generated in Well 1 (e.g., due to an error in a PCR reaction), but may still be used to positively identify the presence of Target B when combined with an expected 2× intensity level in Well 2.

TABLE 7

| Well 1\Well 2 | 0x | 1x | 2x | 3x | 4x | 5x | 6x |
|---|---|---|---|---|---|---|---|
| 0x | None | None | C | C | C | Invalid | Invalid |
| 1x | None | Invalid | B | C | Invalid | BC | Invalid |
| 2x | Invalid | B | B | B | BC | BC | BC |
| 3x | Invalid | A | B | Invalid | AC | BC | Invalid |
| 4x | A | A | A | AC | AC | AC | Invalid |
| 5x | Invalid | A | Invalid | AB | AC | Invalid | ABC |
| 6x | Invalid | Invalid | AB | AB | AB | ABC | ABC |

In some cases, a single reaction may comprise two measurements, which, when compared, may be used to unambiguously detect any combination of analytes. A sample subset (provided, for example, in a plurality of partitions or in a single sample solution volume) may be contacted with a first plurality of hybridization probes to generate a first cumulative signal measurement that fails to non-degenerately indicate the presence or absence of any combination of a plurality of analytes. The first plurality of hybridization probes may be attached to a fluorophore, each capable of being detected in a first signal channel. Each fluorophore of the first plurality of hybridization probes may be the same fluorophore. Each fluorophore of the first plurality of hybridization probes may be different fluorophores, where all are capable of being detected in the same signal channel. Next, a sample subset (provided, for example, in a plurality of partitions or in a single sample solution volume) may be contacted with a second plurality of hybridization probes to generate a second cumulative signal measurement that fails to non-degenerately indicate the presence or absence of any combination of the plurality of analytes. The second plurality of hybridization probes may be attached to a fluorophore, each capable of being detected in a second signal channel. Each fluorophore of the second plurality of hybridization probes may be the same fluorophore. Each fluorophore of the second plurality of hybridization probes may be different, where all are capable of being detected in the same signal channel. The first cumulative signal measurement may be compared to the second cumulative signal measurement, thereby non-degenerately indicating the presence of any combination of the plurality of analytes. In some cases, more than one additional cumulative signal measurement is necessary to resolve an ambiguity of a first cumulative signal measurement. Two, three, four, or more additional measurements may be required, such that only the comparison of all signal measurements non-degenerately indicates the presence of any combination of a plurality of analytes.

Figure 5:
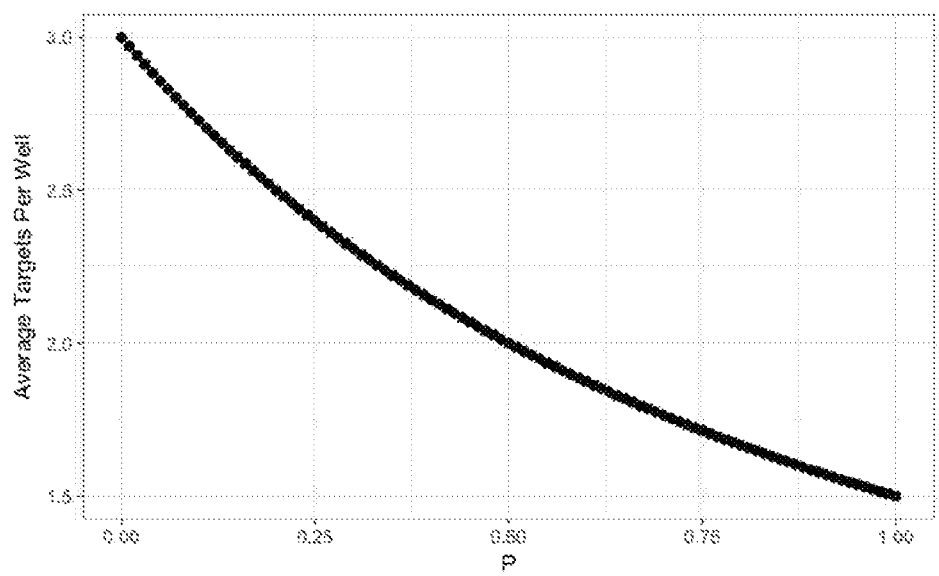
FIG. 5 shows a graph plotting, for an assay for measuring three target analytes from a sample, the average targets per well needed to non-degenerately measure all three analytes relative to a given probability (P) value that only a third target or a first and second target, but not all three, will be present in the sample.

FIG. 5 shows the average number of targets per well needed to non-degenerately resolve three analytes using seven discrete intensity levels (0×-6×), where P is the probability of only a third analyte (e.g., Target C) or a first and second analyte (e.g., Targets A and B) being present in a given sample. When P=0, all three targets can be resolved using a single well. When P=1, 1.5 targets can be resolved per well, such that all three targets can be resolved using two wells. For P<0.5, it is possible to exceed Shannon information bandwidth limits for non-degenerate measurement of targets using only seven discrete intensity levels.

A second reaction may be run in parallel with a first reaction. A second reaction may be run subsequent to the first reaction. In some cases, a second reaction is run only in a case where the first reaction comprises a degeneracy. For example, a first reaction from a first sample may generate a signal measurement which can be unambiguously assigned to a given combination of analytes, such that a second reaction is not necessary. However, a first reaction from a second sample may generate a signal measurement which cannot be unambiguously assigned to a given combination of analytes (e.g., may represent multiple potential analytes combinations), thereby necessitating the use of a second measurement to resolve the ambiguity.

Table 8 shows an example encoding scheme for 22 analytes, where one analyte is a common viral gene and the other 21 analytes are viral genes rarely present in an individual.

TABLE 8

Reaction 1

| Intensity (x) | Encoding Scheme | All codes | Next step |
|---|---|---|---|
| 7 | | AP\|AQ\|AR\|AS\|AT\|AU\|AV | Reflex panel 3 |
| 6 | PQRSTUV | P\|Q\|R\|S\|T\|U\|V | Reflex panel 3 |
| 5 | | AI\|AJ\|AK\|AL\|AM\|AN\|AO | Reflex panel 2 |
| 4 | IJKLMNO | I\|J\|K\|L\|M\|N\|O | Reflex panel 2 |
| 3 | | AB\|AC\|AD\|AE\|AF\|AG\|AH | Reflex panel 1 |
| 2 | BCDEFGH | B\|C\|D\|E\|F\|G\|H | Reflex panel 1 |
| 1 | A | A | A is present |
| 0 | | | No targets |

Depending on the results of the first reaction, an additional reaction ("Reflex panel") may be selected to resolve any degeneracy. Tables 9-11 show three additional reactions which could be used to resolve a degeneracy of Reaction 1. Importantly, only one additional reaction is needed to fully resolve the presence of any of the 21 rare genes.

TABLE 9

Reflex Panel 1

| Intensity (x) | Encoding Scheme | If Reaction 1 Intensity = 3x | If Reaction 1 Intensity = 2x |
|---|---|---|---|
| 7 | H | AH | H |
| 6 | G | AG | G |
| 5 | F | AF | F |
| 4 | E | AE | E |
| 3 | D | AD | D |
| 2 | C | AC | C |
| 1 | B | AB | B |
| 0 | ( ) | (Error, multiple rare targets present) | |

TABLE 10

Reflex Panel 2

| Intensity (x) | Encoding Scheme | If Reaction 1 Intensity = 5x | If Reaction 1 Intensity = 4x |
|---|---|---|---|
| 7 | O | AO | O |
| 6 | N | AN | N |
| 5 | M | AM | M |
| 4 | L | AL | L |
| 3 | K | AK | K |
| 2 | J | AJ | J |
| 1 | I | AI | I |
| 0 | ( ) | (Error, multiple rare targets present) | |

TABLE 11

Reflex Panel 3

| Intensity (x) | Encoding Scheme | If Reaction 1 Intensity = 7x | If Reaction 1 Intensity = 6x |
|---|---|---|---|
| 7 | V | AV | V |
| 6 | U | AU | U |
| 5 | T | AT | T |
| 4 | S | AS | S |
| 3 | R | AR | R |

TABLE 11-continued

Reflex Panel 3

| Intensity (x) | Encoding Scheme | If Reaction 1 Intensity = 7x | If Reaction 1 Intensity = 6x |
|---|---|---|---|
| 2 | Q | AQ | Q |
| 1 | P | AP | P |
| 0 | ( ) | (Error, multiple rare targets present) | |

Sidon Sequence

In some aspects, methods of the present disclosure are used to identify a number of analytes from a sample, where no more than a given number of analytes are expected to be present in the sample. For example, methods may be used to detect polynucleotide analytes corresponding to rare mutations or rare diseases. In these examples, more efficient coding schemes can be employed. For example, if only up to two targets are expected to be present in any given sample, a Sidon coding sequence can be used. A Sidon sequence is a sequence of natural numbers A={a0, a1, a2, . . . } in which the sum of any pair of numbers ai+aj (i≠j) within the set is unique. A valid Sidon sequence inclusive of 0 will result in any pairwise combination of targets being unique to any combination of 0 and a single target, satisfying the requirements for unique encoding of zero, one, or two targets. Table 12 shows examples of Sidon sequences.

TABLE 12

| Sequence | Notes |
|---|---|
| 1, 2, 4, 8 | Sidon Sequence, also optimal non-degenerate coding |
| 1, 2, 4, 7 | Sidon Sequence, conflict with one, three-target combination (1 + 2 + 4 = 7) |

Figure 6:
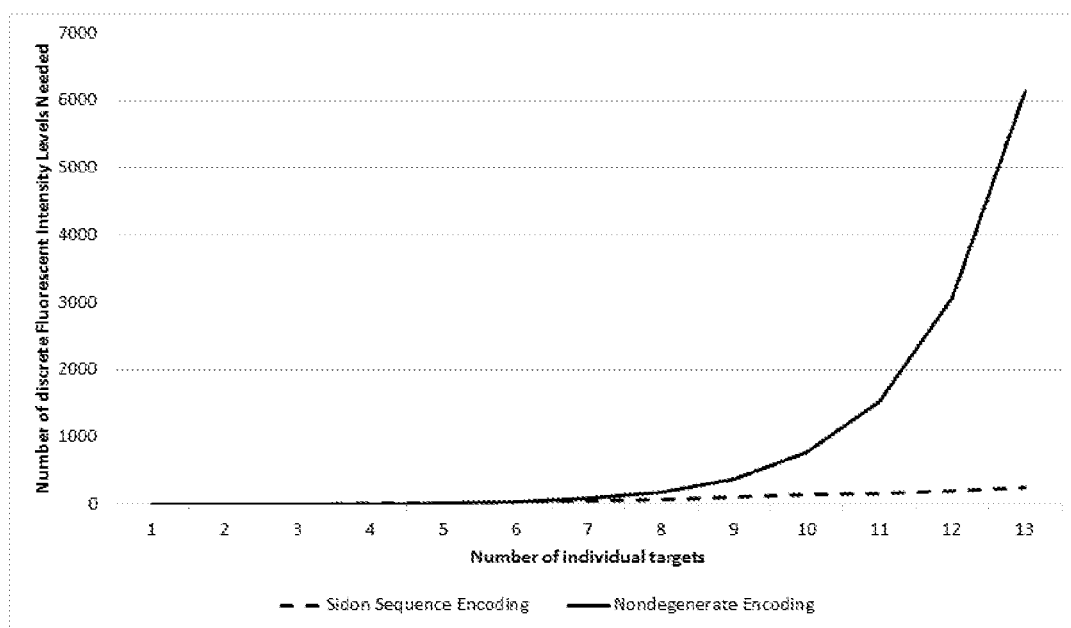
FIG. 6 shows the number of discrete fluorescent levels needed to non-degenerately measure a given number of targets using either a fully nondegenerate encoding scheme, or a Sidon sequence encoding scheme.

Golomb ruler is a set of numbers in integer positions along a sparse ruler such that the distance between any two pairs of marks is unique. All Sidon sequences are Golomb rulers and all Golomb rulers are Sidon sequences. Optimally short Golomb rulers have been tabulated for an order up to 27. Optimal Golomb rulers are inclusive of zero and are guaranteed to be conflict-free up to two targets. As one example, consider a fluorescence measurement with an 8-bit sensor with 256 discrete levels. In the maximally dense non-degenerate coding, 8 targets can be uniquely resolved by encoding the targets as the set A={1, 2, 4, 8, 16, 32, 64, 128}. Using a Golomb Ruler-based degenerate coding scheme, 13 targets can be uniquely encoded as the set A={4, 6, 20, 35, 52, 59, 77, 78, 86, 89, 99, 122, 127}. Every combination of one or two targets in this set is unique, and a maximum value of (122+127) is 249, below the 256 value threshold in the example sensor. As seen in Table 13, this encoding is more efficient at higher levels of target multiplexing. An optimal Golomb ruler may or may not be not be the most dense encoding for a given application. For example, for four targets, a coding of [1,2,4,7] could be used. Additionally, FIG. 6 shows that the growth rate of the number of intensity levels needed per target is now sub-exponential, allowing significant gains in coding density. The disclosed methods can be extended to defining spaces for up to three, four, or more targets across two, three, or more independent measurement channels to ensure an appropriate rate for correct calls for the application, either within the same reaction or in one or more additional reactions.

TABLE 13

| Targets encoded | Sidon Sequence | # levels needed for two targets (Sidon) | Non degenerate coding | # levels needed for two targets (nondegenerate) |
|---|---|---|---|---|
| 1 | 0, 1 | 1 | 0, 1 | 1 |
| 2 | 0, 1, 3 | 4 | 0, 1, 2 | 3 |
| 3 | 0, 1, 4, 6 | 10 | 0, 1, 2, 4 | 6 |
| 4 | 0, 1, 4, 9, 11 | 20 | 0, 1, 2, 4, 8 | 12 |
| 5 | 0, 1, 4, 10, 12, 17 | 29 | 0, 1, 2, 4, 8, 16 | 24 |
| 6 | 0, 1, 4, 10, 18, 23, 25 | 48 | 0, 1, 2, 4, 8, 16, 32 | 48 |
| 7 | 0, 1, 4, 9, 15, 22, 32, 34 | 66 | 0, 1, 2, 4, 8, 16, 32, 64 | 96 |
| 8 | 0, 1, 5, 12, 25, 27, 35, 41, 44 | 85 | 0, 1, 2, 4, 8, 16, 32, 64, 128 | 192 |
| 9 | 0, 1, 6, 10, 23, 26, 34, 41, 53, 55 | 108 | 0, 1, 2, 4, 8, 16, 32, 64, 128, 256 | 384 |
| 10 | 0, 1, 4, 13, 28, 33, 47, 54, 64, 70, 72 | 142 | 0, 1, 2, 4, 8, 16, 32, 64, 128, 256, 512 | 768 |
| 11 | 0, 2, 6, 24, 29, 40, 43, 55, 68, 75, 76, 85 | 161 | 0, 1, 2, 4, 16, 32, 64, 128, 256, 512, 1024 | 1536 |
| 12 | 0, 2, 5, 25, 37, 43, 59, 70, 85, 89, 98, 99, 106 | 205 | 0, 1, 2, 4, 8, 16, 32, 64, 128, 256, 512, 1024, 2048 | 3072 |
| 13 | 0, 4, 6, 20, 35, 52, 59, 77, 78, 86, 89, 99, 122, 127 | 249 | 0, 1, 2, 4, 8, 16, 32, 64, 128, 256, 512, 1024, 2048, 4096 | 6144 |

In some cases, compositions are provided comprising a plurality of hybridization probes, each corresponding to one of a plurality of polynucleotide analytes. A composition may comprise a given amount of each hybridization probe, such that when each hybridization probe is excited and contacted with its corresponding polynucleotide analyte, a cumulative intensity signal is generated, wherein a cumulative signal measurement generated from the cumulative intensity signal forms a Sidon sequence. A composition may comprise 3, 4, 5, 6, 7, 8, 9, 10, 11, 12, 13, 14, 15, 20, or more hybridization probes. Each hybridization probe in a composition may be at a different concentration. The concentration of each hybridization probe in a composition may form a Sidon sequence. For example, a composition may comprise seven hybridization probes, where a first hybridization probe at a concentration of 1×, a second hybridization probe is at a concentration of 4×, a third hybridization probe is at a concentration of 9×, a fourth hybridization probe is at a concentration of 15×, a fifth hybridization probe is at a concentration of 22×, a sixth hybridization probe is at a concentration of 32×, and a seventh hybridization probe is at a concentration of 34×.

Reactions

Methods of the present disclosure may comprise one or more reactions. A reaction may comprise contacting one or more analytes with one or more hybridization probes. A reaction may comprise nucleic acid extension. A reaction may comprise nucleic acid amplification. Nucleic acid amplification may comprise, for example, linear amplification, isothermal amplification, or polymerase chain reaction (PCR). Various methods of nucleic acid amplification may be used in the reactions of the present disclosure. In some cases, a reaction comprises quantitative PCR (qPCR). In some cases, a reaction comprises digital PCR (e.g., droplet digital PCR).

A reaction may generate one or more signals. A reaction may generate a cumulative intensity signal comprising a sum of multiple signals. A signal may be a fluorescent signal. A signal may be generated by a hybridization probe. For example, excitation of a hybridization probe comprising a luminescent signal tag may generate a signal. A signal may be generated by a fluorophore. A fluorophore may generate a signal upon release from a hybridization probe. A reaction may comprise excitation of a fluorophore. A reaction may comprise signal detection. A reaction may comprise detecting emission from a fluorophore.

A reaction may comprise contacting polynucleotide analytes with one or more hybridization probes. A reaction may comprise contacting a sample solution volume with a plurality of hybridization probes, each corresponding to one of a plurality of polynucleotide analytes, to generate a cumulative signal measurement comprising one or more signals generated from the plurality of hybridization probes. In some cases, a cumulative signal measurement from a single reaction fails to non-degenerately identify the presence or absence of any combination of a plurality of polynucleotide analytes. As disclosed herein, two or more cumulative signal measurements may be compared, thereby non-degenerately indicating the presence or absence of a plurality of analytes, in any combination of presence or absence.

Methods of the present disclosure may comprise any number of reactions. A method may comprise at least 1, 2, 3, 4, 5, or more reactions. In some cases, the disclosed methods comprise only two reactions. In some cases, the disclosed methods comprise a single reaction.

Partitioning

Methods of the present disclosure may comprise partitioning a subset of a sample (e.g., comprising polynucleotide analytes), hybridization probes, and, in some cases, additional reagents into a plurality of partitions. A partition may be a droplet. A partition may be an emulsion. A partition may be a well. A partition may be a microwell. Partitioning may be performed using a microfluidic device. In some cases, partitioning is performed using a droplet generator. Partitioning may comprise dividing a mixture (e.g., a mixture comprising polynucleotide analytes, and nucleic acid probes) into water-in-oil droplets. A droplet may comprise one or more polynucleotide analytes. A droplet may comprise a single polynucleotide analyte. A droplet may comprise two or more polynucleotide analyte. A droplet may comprise no polynucleotide analyte. Each droplet of a plurality of droplets may generate a signal. A cumulative signal measurement may comprise the signal(s) generated from each of a plurality of droplets comprising a subset of a sample.

Hybridization Probes

A hybridization probe may be an oligonucleotide probe. A hybridization probe may be a nucleic acid complementary to a region of a given nucleic acid target or analyte. Each hybridization probe used in the methods and assays of the presence disclosure may comprise at least one fluorophore. A fluorophore may be selected from any number of fluorophores. A fluorophore may be selected from three, four, five, six, seven, eight, nine, or ten fluorophores, or more. One or more hybridization probes used in a single reaction may comprise the same fluorophore. In some cases, all hybridization probes used in a single reaction comprise the same fluorophore. Each hybridization probe may, when excited and contacted with its corresponding analyte, generate a signal. A signal may be a fluorescent signal. A cumulative signal measurement may comprise one or more signals generated from one or more hybridization probes.

A hybridization probe may comprise a signal tag. A signal tag may comprise a means of generating a signal such as, for example, a fluorophore. The fluorophore may be, for example, FAM, TET, HEX, JOE, Cy3, or Cy5. A hybridization probe may further comprise one or more quenchers. A quencher may inhibit (i.e., quench) signal generation from a fluorophore. A quencher may be, for example, TAMRA, BHQ-1, BHQ-2, or Dabcy. In some cases, a hybridization probe is a hydrolysis probe. A hydrolysis probe may be, for example, a TaqMan® probe (Applied Biosystems™).

A hybridization probe may correspond to a polynucleotide analyte. For example, a hybridization probe may have complementarity and/or homology to a polynucleotide analyte. A hybridization probe may comprise a region which is complementary or homologous to a region of a polynucleotide analyte. A hybridization probe corresponding to a polynucleotide analyte may be capable of binding to the polynucleotide analyte under appropriate conditions (e.g., temperature conditions, buffer conditions. etc). For example, a hybridization probe may be capable of binding to a polynucleotide analyte under conditions appropriate for polymerase chain reaction. A hybridization probe may correspond to an oligonucleotide which corresponds to a polynucleotide analyte. For example, an oligonucleotide may be a primer with a region complementary to a polynucleotide analyte and a region complementary to a hybridization probe.

Samples and Analytes

An analyte of the present disclosure may be derived from any source including, for example, viruses, bacterial cells, and eukaryotic cells. An analyte may be a polynucleotide (i.e., nucleic acid) analyte. A polynucleotide analyte may be derived from one or more cells. A cell may be a tumor cell. A cell may be a cell suspected of comprising a viral pathogen. In some cases, a polynucleotide analyte is derived from a cell-free sample (e.g., serum, plasma). A polynucleotide analyte may be cell-free nucleic acid. Cell-free nucleic acid may be, for example, cell-free tumor DNA, cell-free fetal DNA, cell-free RNA, etc. A polynucleotide analyte may comprise deoxyribonucleic acid (DNA). DNA may be any kind of DNA, including genomic DNA. A polynucleotide analyte may be viral DNA. A polynucleotide analyte may comprise ribonucleic acid (RNA). RNA may be any kind of RNA, including messenger RNA, transfer RNA, ribosomal RNA, and microRNA. RNA may be viral RNA. A polynucleotide analyte may comprise a gene whose detection may be useful in diagnosing one or more diseases. A gene may be a viral gene or bacterial gene whose detection may be useful in identifying the presence or absence of a pathogen in a subject. In some cases, the methods of the present disclosure are useful in detecting the presence or absence or one or more infectious agents (e.g., viruses) in a subject. In some cases, the methods of the present disclosure are useful in detecting the relative amount of a fetal nucleic acid in a cell-free nucleic acid sample from a subject, thereby diagnosing the fetus for one or more genetic abnormalities. In some cases, the methods of the present disclosure are useful in detecting the presence or absence of tumor DNA in a cell-free nucleic acid sample from a subject, thereby diagnosing the subject for cancer.

Kits

Also provided herein are kits for detecting the presence or absence of a plurality of analytes in a sample. Kits may include one or more hybridization probes. Hybridization probes may be lyophilized. Hybridization probes may be present at different concentrations. Hybridization probes may comprise a signal tag, which may comprise, for example, a fluorophore and one or more quenchers. Kits may include one or more oligonucleotide primers, for example, for performing PCR. One or more of the oligonucleotide primers may be lyophilized. In some cases, all of the oligonucleotide primers may be lyophilized. Kits may comprise one or more nucleic acid enzymes. A nucleic acid enzyme may be a nucleic acid polymerase. A nucleic acid polymerase may be a deoxyribonucleic acid polymerase. A nucleic acid enzyme may be an RNase. An RNase may be an RNase III. An RNase III may be Dicer. The nucleic acid enzyme may be an endonuclease. An endonuclease may be an endonuclease I. An endonuclease I may be a T7 endonuclease I. Kits may comprise instructions for using any of the foregoing in the methods described herein.

EXAMPLES

Example 1

A mixture of primers, nucleic acid hybridization probes, and polymerase were added to a sample containing one or more synthetic DNA targets for influenza A virus (FluA), respiratory syncytial virus A (RsvA), and/or respiratory syncytial virus B (RsvB). For each unique combination of targets, two qPCR reactions were performed using the primer and probe concentrations shown in Table 14. Each reaction was performed with an Applied Biosystems 7500 Fast Real-Time PCR System using Luna Universal Probe One-Step Enzyme Reaction Mix. Cycling conditions consisted of an initial denaturation of 60 seconds at 95° C. and then cycling parameters of 30 seconds at 95° C. followed by 120 seconds at 57° C. If a target was present, it was present at $10^5$ copies per reaction.

TABLE 14

| | Reaction 1 | | | Reaction 2 | | |
|---|---|---|---|---|---|---|
| | Fluorescent Probe | Forward Primer | Reverse Primer | Fluorescent Probe | Forward Primer | Reverse Primer |
| Rsv A | 300 nM (1x) | 1200 nM | 1200 nM | 1200 nM (4x) | 1200 nM | 1200 nM |
| Rsv B | 600 nM (2x) | 1200 nM | 1200 nM | 600 nM (2x) | 1200 nM | 1200 nM |
| Flu A | 900 nM (3x) | 1200 nM | 1200 nM | | | |

Figure 3:
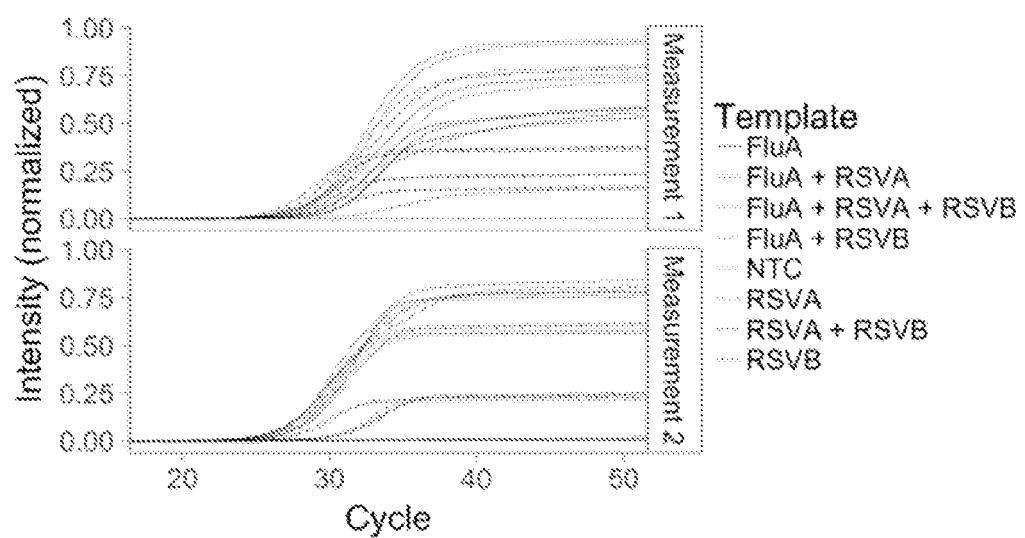
FIG. 3 shows quantitative PCR (qPCR) curves generated from the reactions described in Example 1.
Figure 4:
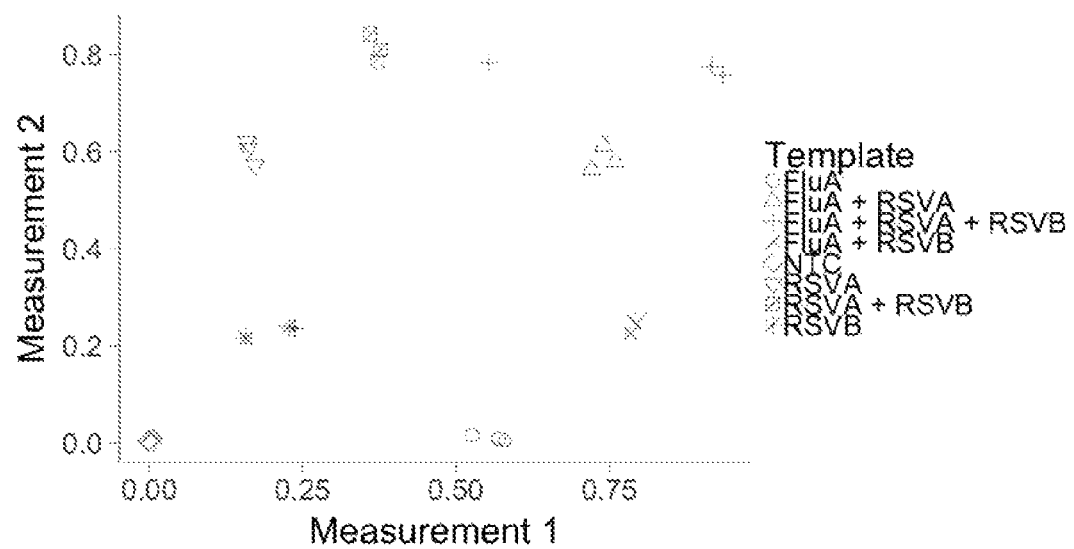
FIG. 4 shows a two-dimensional plot comparing the results from the qPCR curves shown in FIG. 3.

FIG. 3 shows the qPCR curves generated from Reaction 1 (Measurement 1) and Reaction 2 (Measurement 2) from each combination of targets and a no template control (NTC). Data was collected in triplicate for each combination. Measurement 1 and Measurement 2 alone each fail to identify every combination of targets. FIG. 4 shows the results of a comparison of the two measurements as a two dimensional plot of the final intensity for each qPCR curve from FIG. 3. Each unique combination of targets is present at a distinct location in the two dimensional plot, thereby identifying each combination of the targets. The triplicate measurements generate discrete clusters on the plot, enabling accurate error correction. For example, one of the triplicate measurements all three targets (FluA+RSVA+RSVB) exhibited a lower than expected intensity value for measurement 1 but the expected intensity value for measurement 2. The analysis of both reactions allows identification of this data point as a "no-call", which can readily be discarded from analysis. By contrast, this data point may have been incorrectly identified as a different target combination using just a single measurement.

Example 2

A mixture of primers, nucleic acid hybridization probes, and polymerase were added to a sample containing one or more synthetic DNA targets for FluA, influenza B virus (FluB), RsvA, and/or RsvB. Primers and nucleic acid probes labeled with the FAM fluorophore were formulated into a mixture at probe ratios that would generate signals corresponding to the Sidon sequence {1, 2, 4, 7}. PCR curves were then generated on an Applied Biosystems 7500 Fast Real-Time PCR System using Taq polymerase, the primer/probe mix, and $10^5$ copies/reaction of every single and dual target combination. Every experimental condition was run in triplicate. Cycling conditions consisted of an initial denaturation step of 60 seconds at 95° C., and then 45 cycles of 30 seconds at 95° C. followed by 120 seconds at 57° C.

Figure 7:
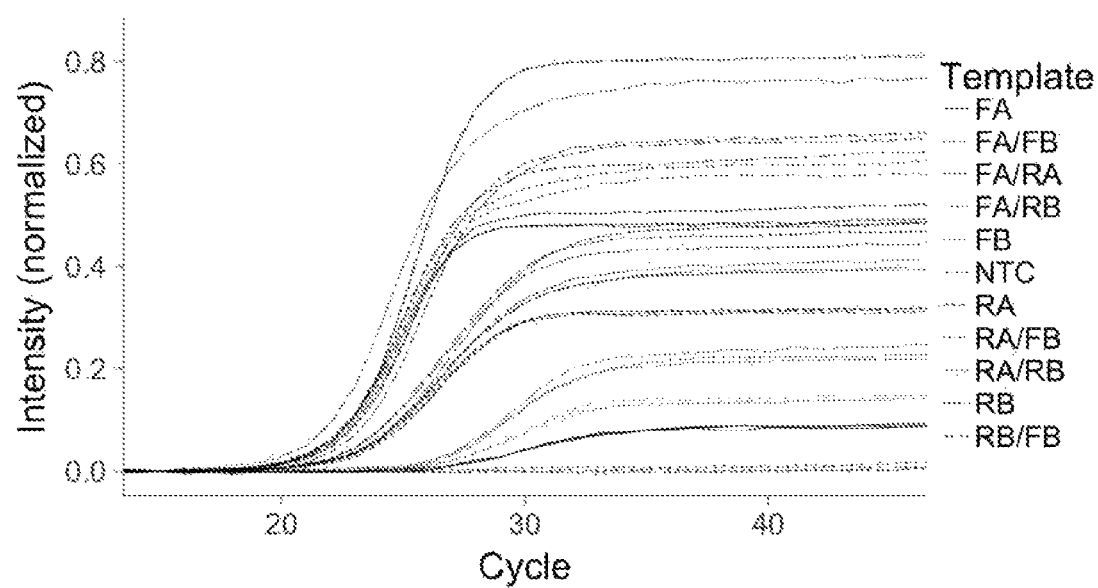
FIG. 7 shows qPCR curves generated from the reactions described in Example 2.
Figure 8:
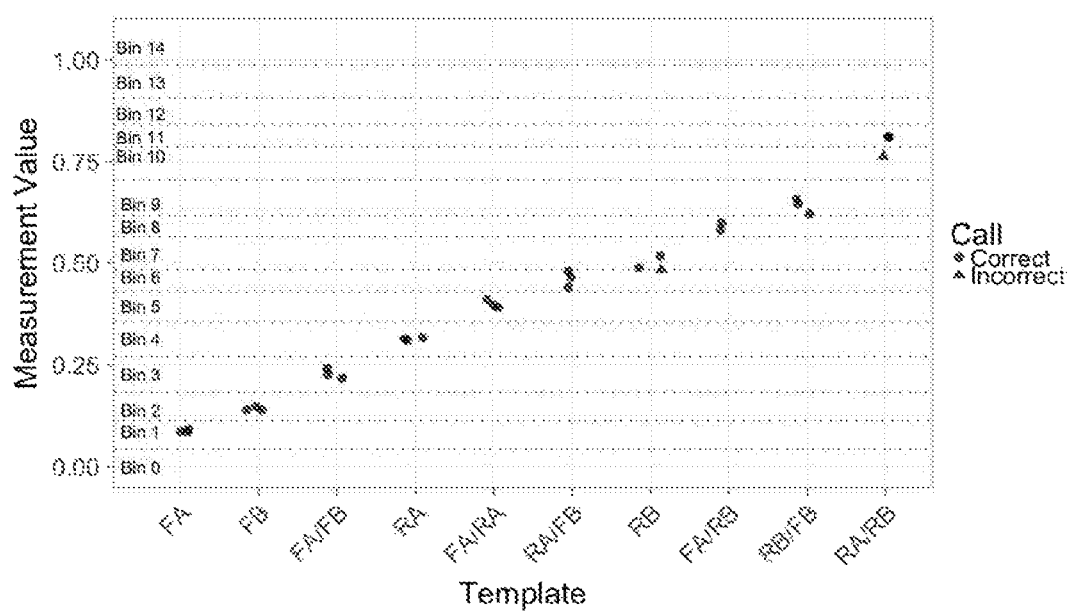
FIG. 8 shows clustering of each replicate for a given target combination, based on the qPCR curves in FIG. 7.

FIG. 7 shows the qPCR curves generated from each of these reactions. Each pair-wise combination of targets generates a discrete end-point fluorescent signal intensity. FIG. 8 shows the clustering of each replicate for a given target combination, separated into distinct bins based on fluorescence intensity. This data shows a 93.1% positive call accuracy rate using this Sidon sequence.

Example 3

Table 15 shows an example respiratory viral panel using a 12-target rolling code scheme. A formulation of primers and hybridization probes, each specific for one of the targets in Table 15, was generated such that signals would be generated corresponding to the scheme in Table 15. To test this scheme, a dilution series of synthetic templates was tested using the formulation.

This encoding method results in a fully non-degenerate solution space for every combination of zero, one, two, or three targets, while some combinations of four or more targets will not be able to be disambiguated. Some examples of ambiguous states are enumerated in Table 16.

TABLE 16

| Targets Present | Ch1 'level' | Ch2 'level' | Ch3 'level' | Ch4 'level' |
|---|---|---|---|---|
| 111100000000 | 4 | 4 | 4 | 4 |
| 000000001111 | 4 | 4 | 4 | 4 |
| 000010101010 | 3 | 3 | 3 | 3 |
| 000001010101 | 3 | 3 | 3 | 3 |
| 110000010001 | 3 | 3 | 4 | 4 |
| 000000101110 | 3 | 3 | 4 | 4 |
| 011010001000 | 3 | 4 | 4 | 3 |
| 000000010111 | 3 | 4 | 4 | 3 |
| 001101000100 | 4 | 4 | 3 | 3 |
| 000010001011 | 4 | 4 | 3 | 3 |
| 100100100010 | 4 | 3 | 3 | 4 |
| 000001001101 | 4 | 3 | 3 | 4 |
| 100000010011 | 3 | 4 | 3 | 4 |
| 001001001100 | 3 | 4 | 3 | 4 |
| 010010001001 | 4 | 3 | 4 | 3 |
| 000100100110 | 4 | 3 | 4 | 3 |

Thus, a sample with the presence of the four targets B, E, I, L could not be distinguished from a sample with the four targets D, G, J, K. To test this method, twelve respiratory viral targets were formulated in this method as shown in Table 17. In this case, the equivalent ambiguous state would be a sample with Adenovirus, Parainfluenza 3, Parainfluenza 1, and RSVA and a sample with RSVB, FluA H1, Metapneumovirus, and FluA Pan marker, which, depending on the expected population of samples, could be assumed to be extremely rare. A dilution series of synthetic templates was tested on this formulation as shown in Table 18.

TABLE 17

| Target | Name | 'Target Presence Code' |
|---|---|---|
| A | Parainfluenza 2 | 100000000000 |
| B | Adenovirus | 010000000000 |
| C | FluA H3 Subtype | 001000000000 |
| D | RSVB | 000100000000 |
| E | Parainfluenza 3 | 000010000000 |
| F | FluB | 000001000000 |

TABLE 15

| Target | "Target Presence Code" | Ch1 Probe(nM) | Ch2 Probe(nM) | Ch3 Probe(nM) | Ch4 Probe(nM) | Ch1 'level' | Ch2 'level' | Ch3 'level' | Ch4 'level' |
|---|---|---|---|---|---|---|---|---|---|
| A | 100000000000 | 0 | 0 | 0 | 100 | 0 | 0 | 0 | 4 |
| B | 010000000000 | 0 | 0 | 100 | 0 | 0 | 0 | 4 | 0 |
| C | 001000000000 | 0 | 100 | 0 | 0 | 0 | 4 | 0 | 0 |
| D | 000100000000 | 100 | 0 | 0 | 0 | 4 | 0 | 0 | 0 |
| E | 000010000000 | 0 | 0 | 0 | 50 | 0 | 0 | 0 | 2 |
| F | 000001000000 | 0 | 0 | 50 | 0 | 0 | 0 | 2 | 0 |
| G | 000000100000 | 0 | 50 | 0 | 0 | 0 | 2 | 0 | 0 |
| H | 000000010000 | 50 | 0 | 0 | 0 | 2 | 0 | 0 | 0 |
| I | 000000001000 | 75 | 0 | 0 | 25 | 3 | 0 | 0 | 1 |
| J | 000000000100 | 0 | 0 | 25 | 75 | 0 | 0 | 1 | 3 |
| K | 000000000010 | 0 | 25 | 75 | 0 | 0 | 1 | 3 | 0 |
| L | 000000000001 | 25 | 75 | 0 | 0 | 1 | 3 | 0 | 0 |

TABLE 17-continued

| Target | Name | 'Target Presence Code' |
|---|---|---|
| G | FluA H1 Subtype | 000000100000 |
| H | Rhinovirus | 000000010000 |
| I | Parainfluenza 1 | 000000001000 |
| J | Metapneumovirus | 000000000100 |
| K | FluA Pan Marker | 000000000010 |
| L | RSVA | 000000000001 |

TABLE 18

| Target | # Copies | Replicates |
|---|---|---|
| A | 40 | 3 |
| A | 400 | 3 |
| A | 4000 | 3 |
| B | 40 | 3 |
| B | 400 | 3 |
| B | 4000 | 3 |
| E | 40 | 3 |
| E | 400 | 3 |
| E | 4000 | 3 |
| F | 40 | 3 |
| F | 400 | 3 |
| F | 4000 | 3 |
| I | 40 | 3 |
| I | 400 | 3 |
| I | 4000 | 3 |
| J | 40 | 3 |
| J | 400 | 3 |
| J | 4000 | 3 |

Figure 9:
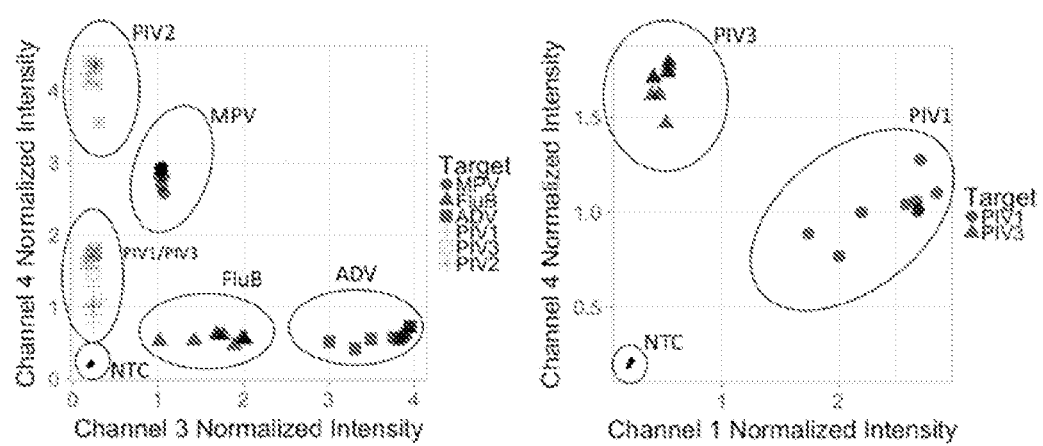
FIG. 9 shows a multidimensional analysis of the qPCR reactions described in Example 3.
Figure 10A:
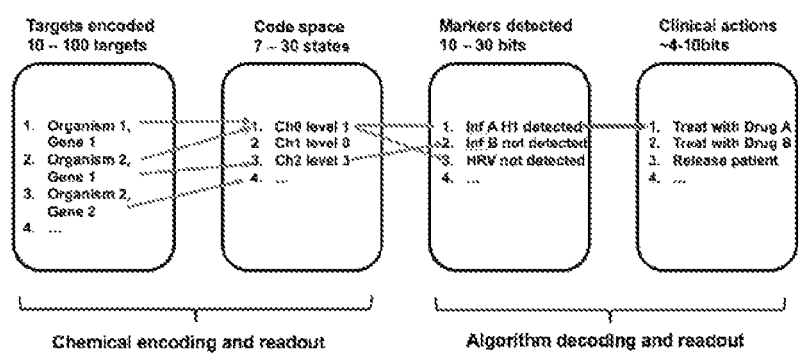
FIGS. 10A and 10B show an example scheme for providing a clinician with information necessary to make an informed clinical decision, without a need for non-degenerately detecting each target analyte from a sample.
Figure 10B:
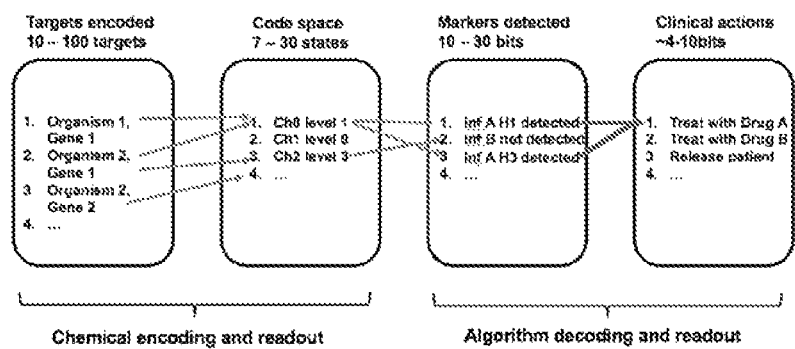

The primer/probe mix was combined with synthetic template at the target combinations shown in Table 18 and run with a commercially available Taq polymerase on an Applied Biosystems Viia7 system for 70 cycles of 15 seconds at 95° C. and 2 minutes at 60° C. following an initial denaturation of 60 seconds at 95° C. Target calls were assigned by clusters in the multidimensional fluorescent intensity space, the results of which as shown in FIG. 9. Any such simple decoding algorithm can be constructed using many methods of classifying targets.

Example 4

Figure 11:
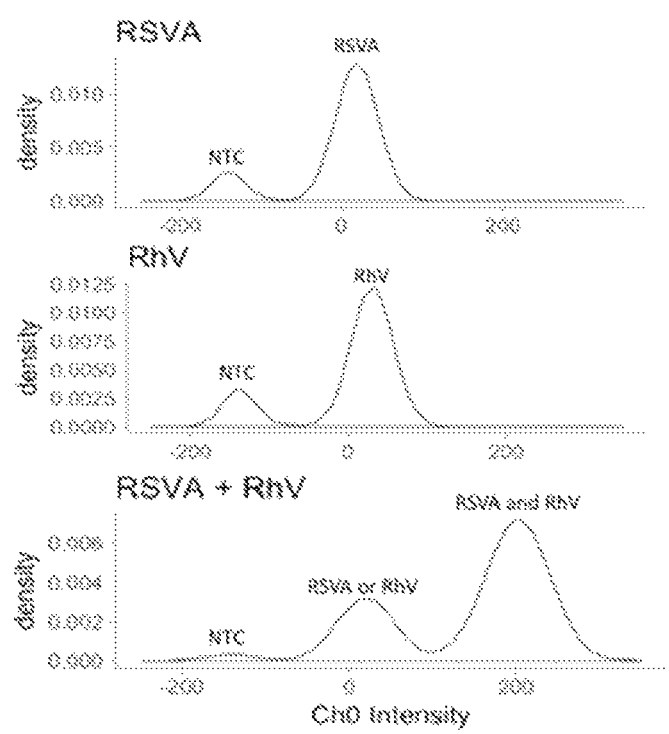
FIG. 11 shows the results of the experiment described in Example 4.

A formulation was constructed such that the fluorescence intensity due to the presence of either target in a droplet on a BioRad CX100 system mapped to the same location on fluorescent channel 1 of the system (FAM). A test was run with wells containing either RSVA synthetic template at approximately 20,000 copies, Rhinovirus (RhV) synthetic template at approximately 20,000 copies, or both. The results of this experiment are shown in FIG. 11. The data generated cannot be used to disambiguate between the two targets, however if the two targets did not need to be disambiguated in order to make a clinical decision, a clinical decision could be made based on these results despite the ambiguity.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of unambiguously detecting the presence or absence of at least three polynucleotide analytes in a sample, in any combination of presence or absence, the method comprising:
   (a) providing a first reaction mixture comprising the sample and a first plurality of hybridization probes, wherein a hybridization probe of the first plurality of hybridization probes is specific for an analyte of the at least three polynucleotide analytes, wherein the first plurality of hybridization probes comprises hybridization probes specific for at least two of the at least three polynucleotide analytes, wherein the hybridization probes specific for the at least two of the at least three polynucleotide analytes comprise a first fluorophore that is identical for the first plurality of hybridization probes, wherein a first hybridization probe generates a first signal intensity in an amplification reaction, wherein a second hybridization probe generates a second signal intensity in the amplification reaction different from the first signal intensity, wherein a signal intensity of the first reaction mixture in the amplification reaction corresponds to a combination of presence or absence of the at least three polynucleotide analytes, wherein at least one combination of analytes produces a same signal intensity as a second combination of analytes, thereby producing an ambiguity between at least two combinations of analytes;
   (b) providing a second reaction mixture comprising the sample and a second plurality of hybridization probes, wherein a hybridization probe of the second plurality of hybridization probes is specific for an analyte of the at least three polynucleotide analytes, wherein the second plurality of hybridization probes comprises hybridization probes specific for at least two of the at least three polynucleotide analytes, wherein the hybridization probes specific for the at least two of the at least three polynucleotide analytes comprise a second fluorophore that is identical for the second plurality of hybridization probes, wherein a third hybridization probe generates a third signal intensity in an amplification reaction, wherein a fourth hybridization probe generates a fourth signal intensity in the amplification reaction different from the third signal intensity, wherein a signal intensity of the second reaction mixture in the amplification reaction corresponds to a combination of presence or absence of the at least three polynucleotide analytes;
   (c) generating the signal intensity of the first reaction mixture using a first amplification reaction and generating the signal intensity of the second reaction mixture using a second amplification reaction; and
   (d) processing the signal intensity of the first reaction mixture and the signal intensity of the second reaction mixture to generate a combined output, wherein the combined output unambiguously identifies a given combination of presence or absence of the at least three polynucleotide analytes in the sample, thereby resolving the ambiguity.

2. The method of claim 1, wherein a number of unique hybridization probes in the first plurality of hybridization probes is less than or equal to a number of unique polynucleotide analytes in the at least three polynucleotide analytes.

3. The method of claim 1, wherein a number of unique hybridization probes in the second plurality of hybridization probes is less than or equal to a number of unique polynucleotide analytes in the at least three polynucleotide analytes.

4. The method of claim 1, wherein the first plurality of hybridization probes and the second plurality of hybridization probes are oligonucleotide probes.

5. The method of claim 1, wherein the method does not require any step of immobilization of the at least three polynucleotide analytes, microscopy, flow cytometry, physical separation of the at least three polynucleotide analytes, mass spectrometry, or melting curve analysis.

6. The method of claim 1, wherein each hybridization probe of the first plurality of hybridization probes and the second plurality of hybridization probes comprises a fluorophore capable of being detected in the same optical channel.

7. The method of claim 1, wherein each hybridization probe of the first plurality of hybridization probes and the second plurality of hybridization probes comprises an identical fluorophore.

8. The method of claim 1, wherein each hybridization probe of the first plurality of hybridization probes and the second plurality of hybridization probes is provided at a different concentration.

9. The method of claim 1, wherein the at least three polynucleotide analytes are at least seven polynucleotide analytes.

10. The method of claim 1, wherein the method does not require any step of immobilization of the polynucleotide analytes, microscopy, flow cytometry, physical separation of the polynucleotide analytes, mass spectrometry, or melting curve analysis.

11. The method of claim 1, wherein each of the first plurality of hybridization probes and the second plurality of hybridization probes corresponds to one of the at least three polynucleotide analytes.

12. The method of claim 1, wherein each of the first plurality of hybridization probes and the second plurality of hybridization probes has complementarity to one of the at least three polynucleotide analytes.

13. The method of claim 1, wherein the processing further comprises comparing said combined output to an expected value.

14. The method of claim 1, wherein the first amplification reaction or second amplification reaction comprises a digital polymerase chain reaction.

15. The method of claim 14, wherein prior to (c), the first reaction mixture or the second reaction mixture is divided into a plurality of partitions.

16. The method of claim 15, wherein the plurality of partitions is a plurality of wells.

17. The method of claim 1, wherein the first amplification reaction or second amplification reaction comprises a polymerase chain reaction.

* * * * *